US012692309B2

(12) United States Patent
Qu et al.

(10) Patent No.: US 12,692,309 B2
(45) Date of Patent: Jul. 28, 2026

(54) ANTI-CLDN ANTIBODY AND PHARMACEUTICAL COMPOSITION THEREOF AND DETECTION METHOD THEREFOR

(71) Applicant: QURE BIOTECHNOLOGY (SHANGHAI) CO., LTD., Shanghai (CN)

(72) Inventors: Xiangdong Qu, Shanghai (CN); Qin Pan, Shanghai (CN); Houcong Jin, Shanghai (CN); Yejie Du, Shanghai (CN); Han Zheng, Shanghai (CN)

(73) Assignee: QURE BIOTECHNOLOGY (SHANGHAI) CO., LTD., Shanghai (CN)

( * ) Notice: Subject to any disclaimer, the term of this patent is extended or adjusted under 35 U.S.C. 154(b) by 370 days.

(21) Appl. No.: 17/611,370

(22) PCT Filed: Apr. 7, 2020

(86) PCT No.: PCT/CN2020/083570
§ 371 (c)(1),
(2) Date: Nov. 15, 2021

(87) PCT Pub. No.: WO2020/228447
PCT Pub. Date: Nov. 19, 2020

(65) Prior Publication Data
US 2022/0235128 A1     Jul. 28, 2022

(30) Foreign Application Priority Data
May 16, 2019     (CN) ......................... 201910410255.8

(51) Int. Cl.
C07K 16/28     (2006.01)
A61K 39/00     (2006.01)
A61P 35/00     (2006.01)
G01N 33/575     (2026.01)

(52) U.S. Cl.
CPC ............. *C07K 16/28* (2013.01); *A61P 35/00* (2018.01); *G01N 33/5759* (2026.01); *A61K 39/00* (2013.01); *C07K 2317/51* (2013.01); *C07K 2317/515* (2013.01); *C07K 2317/565* (2013.01); *C07K 2317/94* (2013.01)

(58) Field of Classification Search
CPC ................ C07K 16/28; C07K 2317/51; C07K 2317/515; C07K 2317/565; A61P 35/00; G01N 33/6854; G01N 33/68
See application file for complete search history.

(56) References Cited

U.S. PATENT DOCUMENTS 5,595,756 A * 1/1997 Bally .................. A61K 9/1272
264/4.1
2018/0319894 A1 11/2018 Singh

FOREIGN PATENT DOCUMENTS

| CN | 105073777 A | 11/2015 |
|---|---|---|
| CN | 105189554 A | 12/2015 |
| CN | 107667118 A | 2/2018 |
| JP | 2016517447 A | 6/2016 |
| RU | 2642305 C2 | 1/2018 |
| WO | 2014146778 A1 | 9/2014 |
| WO | 2018/054973 A1 | 3/2018 |

OTHER PUBLICATIONS

Sporn et al., Chemoprevention of Cancer, 2000, Carcinogenesis, vol. 21, No. 3, pp. 525-530) (Year: 2000).*
Auerbach et al., Angiogenesis assays: Problems and pitfalls, 2000, Cancer and Metastasis Reviews, vol. 19, pp. 167-172 ( Year: 2000).*
Hogenesch et al., Challenges in pre-clinical testing of anti-cancer drugs in cell culture and in animal models, 2012, Journal of Control Release, vol. 164, Issue 2, pp. 183-186 (Year: 2012).*
Jackson ImmunoResearch, Direct and Indirect Western Blotting, 2016, Jackson ImmunoResearch Laboratories, p. 1-3 (Year: 2016).*
Tureci, Ozlem et al.; "Characterization of zolbetuximab in pancreatic cancer models", ONCOIMMUNOLOGY; vol. 8, No. 1; Year: 2019; pp. 1-10; ISSN: 0004905364.
Nishi, Kenji; Nagoya International Patent Firm, office action of Japanese Patent application No. 2021-568696, Oct. 20, 2022.
Federal Service for Intellectual Property; Office action of Federal State Budgetary Institution Application No. 2021136071-10(076051); Apr. 7, 2020.
Singh, Prabhsimranjot et al.; "Anti-claudin 18.2 antibody as new targeted therapy for advanced gastric cancer"; Journal of Hematology & Oncology; vol. 10, No. 105; May 12, 2017; pp. 1-5.

* cited by examiner

*Primary Examiner* — Jeffrey Stucker
*Assistant Examiner* — Brittney E Donoghue
(74) *Attorney, Agent, or Firm* — NKL Law; Bin Lu; Allen Xue

(57) ABSTRACT

Provided are an anti-CLDN18.2 antibody and a pharmaceutical composition thereof and a detection method therefor, wherein the heavy chain of the antibody is selected from any one of SEQ ID NOs: 1-7 or SEQ ID NOs: 15-30, and the light chain of the antibody is selected from any one of SEQ ID NOs: 8-14 or SEQ ID NOs: 31-46. The ability of the antibody to bind to cell lines and tumor tissue cells is more powerful than that of the existing antibody IMAB362, and the anti-tumor effect of the antibody is also more powerful than that of the existing antibody IMAB362.

7 Claims, 20 Drawing Sheets
Specification includes a Sequence Listing.

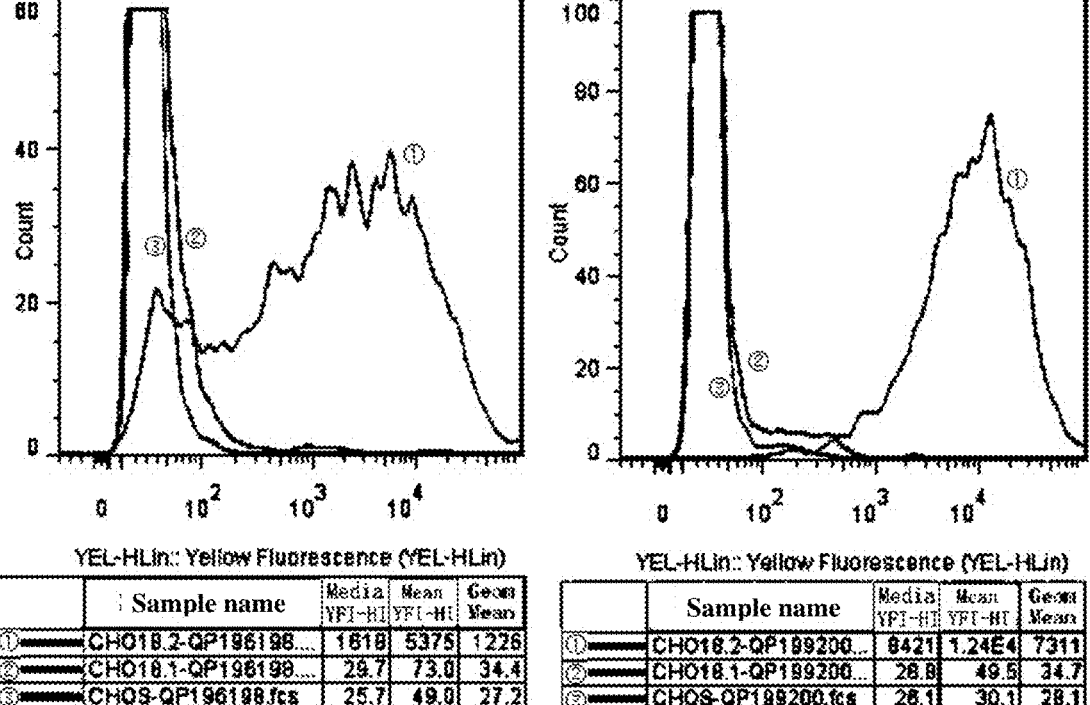
| | Sample name | Media YFI-HI | Mean YFI-HI | Geom Mean |
|---|---|---|---|---|
| ① | CHO18.2-QP196198... | 1618 | 5375 | 1226 |
| ② | CHO18.1-QP196198... | 29.7 | 73.0 | 34.4 |
| ③ | CHOS-QP196198.fcs | 25.7 | 49.0 | 27.2 |
| | Sample name | Media YFI-HI | Mean YFI-HI | Geom Mean |
|---|---|---|---|---|
| ① | CHO18.2-QP199200... | 8421 | 1.24E4 | 7311 |
| ② | CHO18.1-QP199200... | 28.8 | 49.5 | 34.7 |
| ③ | CHOS-QP199200.fcs | 26.1 | 30.1 | 28.1 |
FIG. 1E                    FIG. 1F

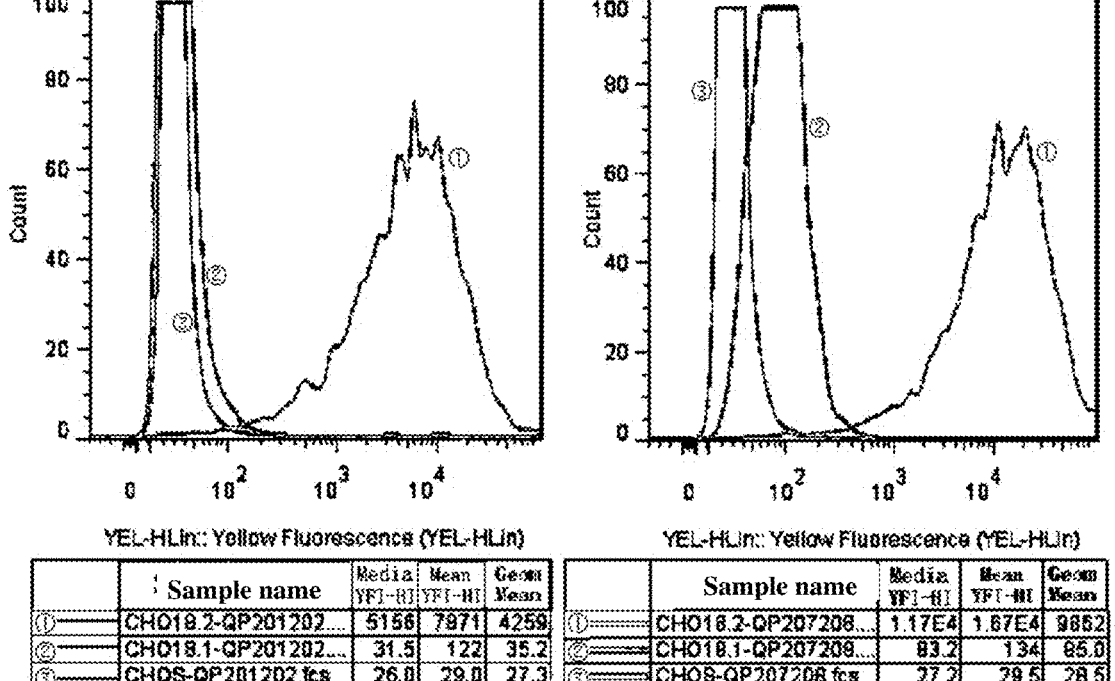
| | Sample name | Media YFI-HI | Mean YFI-HI | Geom Mean |
|---|---|---|---|---|
| ① | CHO18.2-QP201202... | 5156 | 7871 | 4259 |
| ② | CHO18.1-QP201202... | 31.5 | 122 | 35.2 |
| ③ | CHOS-QP201202.fcs | 26.0 | 29.0 | 27.3 |
| | Sample name | Media YFI-HI | Mean YFI-HI | Geom Mean |
|---|---|---|---|---|
| ① | CHO18.2-QP207206... | 1.17E4 | 1.67E4 | 9852 |
| ② | CHO18.1-QP207206... | 83.2 | 134 | 85.0 |
| ③ | CHOS-QP207206.fcs | 37.2 | 29.5 | 28.5 |
FIG. 1G                    FIG. 1H

| Sample name | Media YFI-HI | Mean YFI-HI | Geom Mean |
|---|---|---|---|
| CHO18.2-QP10731074... | 7027 | 1.03E4 | 5978 |
| CHO18.1-QP10731074... | 27.6 | 37.9 | 31.5 |
| CHOS-QP10731074.fcs | 25.3 | 27.9 | 26.8 |

| Sample name | Media YFI-HI | Mean YFI-HI | Geom Mean |
|---|---|---|---|
| CHO18.2-QP10791080... | 1873 | 5372 | 1333 |
| CHO18.1-QP10791080... | 81.6 | 102 | 81.8 |
| CHOS-QP10791080.fcs | 25.3 | 26.8 | 26.1 |

| Sample name | Media YFI-HI | Mean YFI-HI | Geom Mean |
|---|---|---|---|
| CHO18.2-QP10851086... | 6203 | 9873 | 4615 |
| CHO18.1-QP10851086... | 47.6 | 150 | 57.8 |
| CHOS-QP10851086.fcs | 28.1 | 61.0 | 32.7 |

| Sample name | Media YFI-HI | Mean YFI-HI | Geom Mean |
|---|---|---|---|
| CHO18.2-QP10911092... | 7420 | 1.21E4 | 5437 |
| CHO18.1-QP10911092... | 39.8 | 54.7 | 45.0 |
| CHOS-QP10911092.fcs | 28.5 | 32.7 | 29.1 |

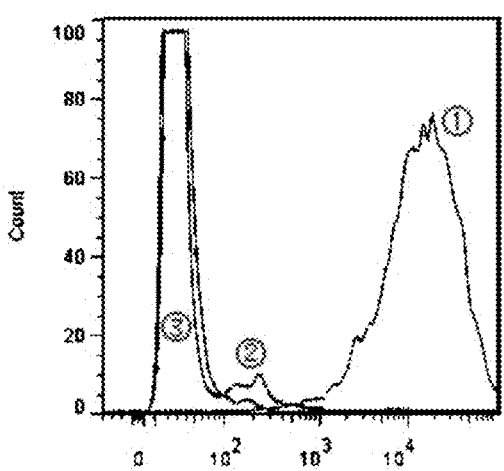
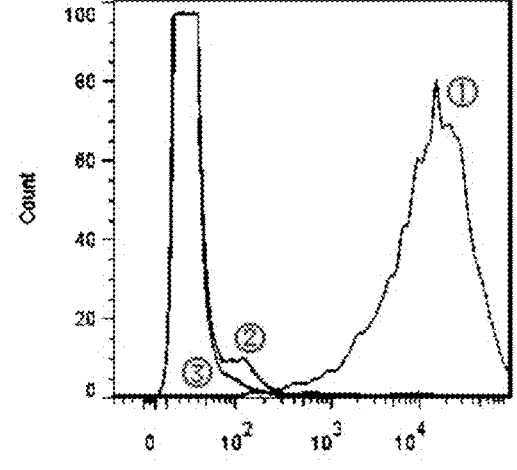
FIG. 3C                        FIG. 3D
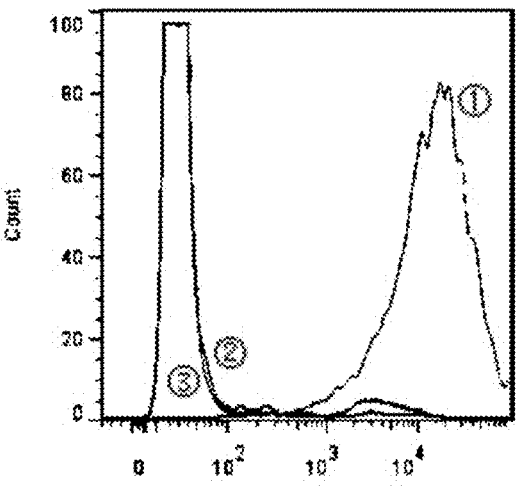
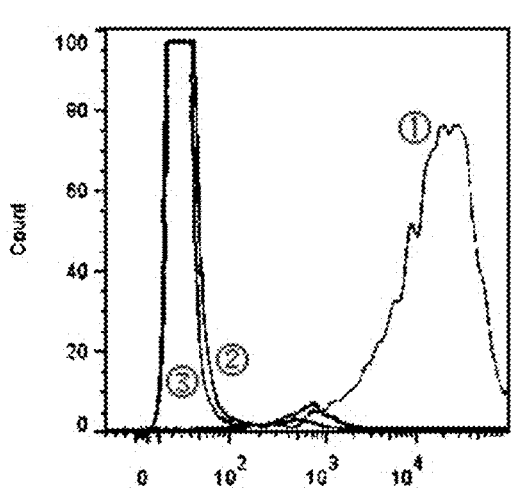
FIG. 3E                        FIG. 3F

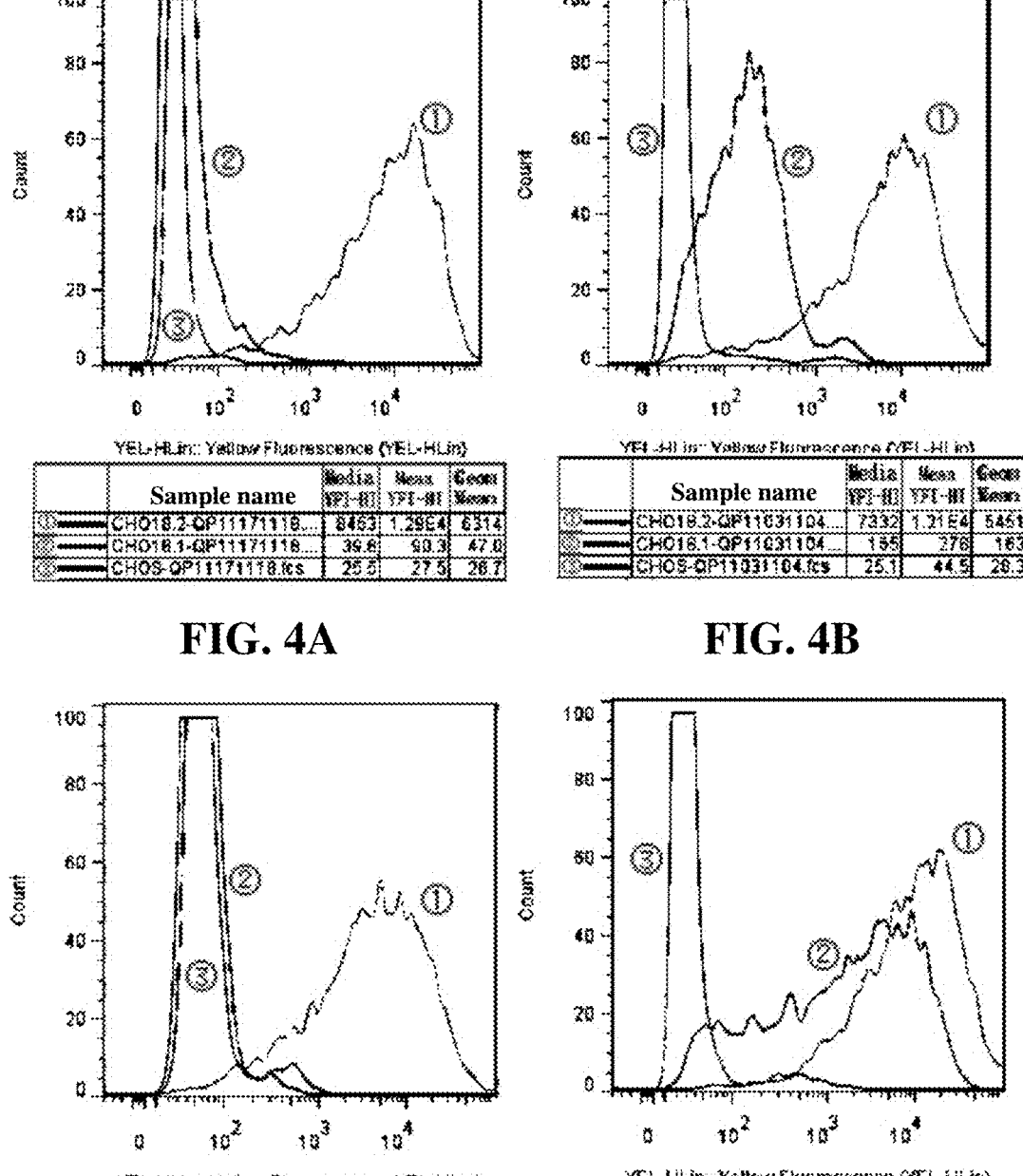
FIG. 4A                    FIG. 4B
FIG. 4C                    FIG. 4D

Hybridoma clone in 293T system

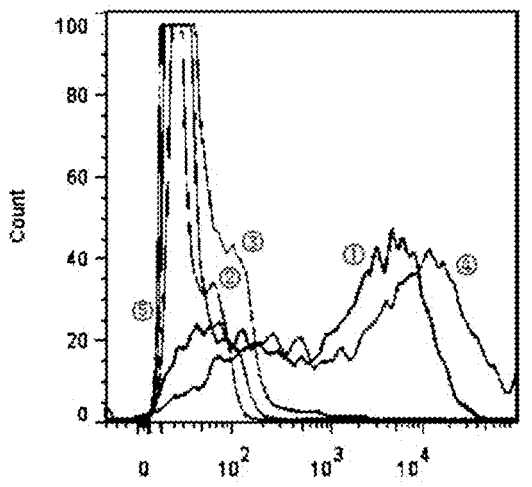

YEL-HLin:: Yellow Fluorescence (YEL-HLin)

| | Sample name | Media YFT-HI | Mean YFT-HI | Geom Mean |
|---|---|---|---|---|
| ① | 293T-QD211-QP024025... | 1476 | 3373 | 837 |
| ② | 293T-QD210-QP024025... | 17.6 | 28.8 | 23.6 |
| ③ | 293T-QD012-QP024025... | 36.8 | 76.4 | 47.6 |
| ④ | 293T-QD010-QP024025... | 3680 | 1.04E4 | 2115 |
| ⑤ | 293T-QP024025.fcs | 23.6 | 32.2 | 28.8 |

FIG. 5A

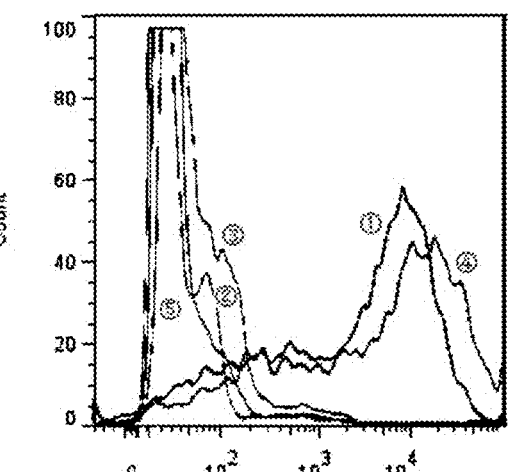

YEL-HLin:: Yellow Fluorescence (YEL-HLin)

| | Sample name | Media YFT-HI | Mean YFT-HI | Geom Mean |
|---|---|---|---|---|
| ① | 293T-QD211-QP188189... | 3948 | 6553 | 1998 |
| ② | 293T-QD210-QP188189... | 20.9 | 282 | 31.5 |
| ③ | 293T-QD012-QP188189... | 42.1 | 534 | 58.5 |
| ④ | 293T-QD010-QP188189... | 5684 | 1.31E4 | 2972 |
| ⑤ | 293T-QP188189.fcs | 25.5 | 378 | 34.7 |

FIG. 5B

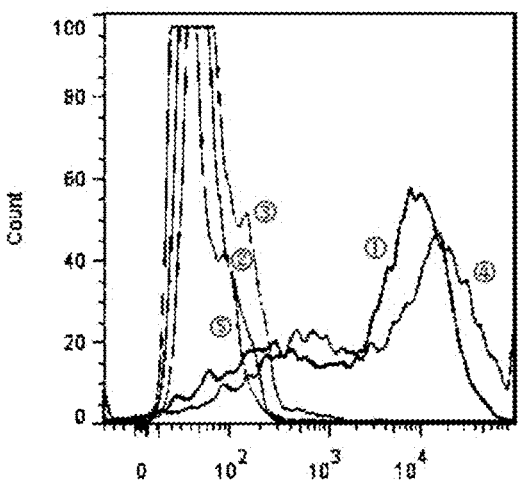

YEL-HLin:: Yellow Fluorescence (YEL-HLin)

| | Sample name | Media YFT-HI | Mean YFT-HI | Geom Mean |
|---|---|---|---|---|
| ① | 293T-QD211-QP190191 | 4356 | 7232 | 2137 |
| ② | 293T-QD210-QP190191 | 35.4 | 48.2 | 41.4 |
| ③ | 293T-QD012-QP190191 | 61.2 | 102 | 71.4 |
| ④ | 293T-QD010-QP190191 | 5720 | 1.36E4 | 3216 |
| ⑤ | 293T-QP190191.fcs | 44.5 | 55.6 | 49.6 |

FIG. 5C

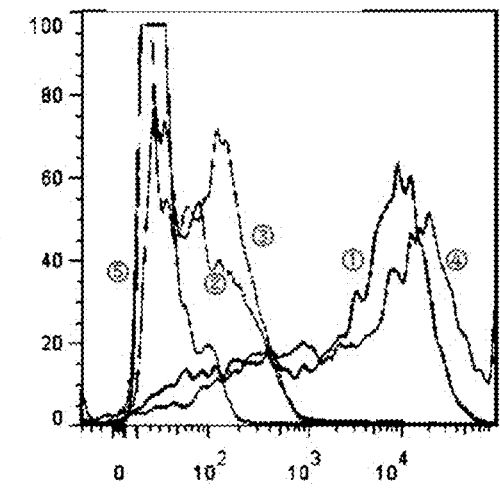

YEL-HLin:: Yellow Fluorescence (YEL-HLin)

| | Sample name | Media YFT-HI | Mean YFT-HI | Geom Mean |
|---|---|---|---|---|
| ① | 293T-QD211-QP192193... | 4401 | 6806 | 2097 |
| ② | 293T-QD210-QP192193... | 53.9 | 97.2 | 62.3 |
| ③ | 293T-QD012-QP192193... | 86.5 | 183 | 86.9 |
| ④ | 293T-QD010-QP192193... | 6531 | 1.42E4 | 3338 |
| ⑤ | 293T-QP192193.fcs | 23.6 | 33.4 | 28.6 |

FIG. 5D

| Sample name | Media YFT-Hl | Mean YFT-Hl | Geom Mean |
|---|---|---|---|
| ① 293T-QD211-QP196198.... | 3383 | 5774 | 1628 |
| ② 293T-QD210-QP196198.... | 18.9 | 43.2 | 26.4 |
| ③ 293T-QD012-QP196198.... | 37.7 | 67.6 | 48.0 |
| ④ 293T-QD010-QP196198.... | 5457 | 1.36E4 | 2861 |
| ⑤ 293T-QP196198.fcs | 22.7 | 31.3 | 28.0 |

| Sample name | Media YFT-Hl | Mean YFT-Hl | Geom Mean |
|---|---|---|---|
| ① 293T-QD211-QP199200.... | 4713 | 7536 | 2340 |
| ② 293T-QD210-QP199200.... | 25.5 | 47.1 | 35.3 |
| ③ 293T-QD012-QP199200.... | 46.0 | 84.9 | 59.1 |
| ④ 293T-QD010-QP199200.... | 8915 | 1.69E4 | 4565 |
| ⑤ 293T-QP199200.fcs | 26.1 | 40.3 | 34.0 |

| Sample name | Media YFT-Hl | Mean YFT-Hl | Geom Mean |
|---|---|---|---|
| ① 293T-QD211-QP201202.... | 4392 | 7504 | 2160 |
| ② 293T-QD210-QP201202.... | 34.3 | 53.1 | 41.2 |
| ③ 293T-QD012-QP201202.... | 64.0 | 109 | 74.6 |
| ④ 293T-QD010-QP201202.... | 9238 | 1.66E4 | 4621 |
| ⑤ 293T-QP201202.fcs | 48.1 | 68.1 | 53.6 |

| Sample name | Media YFT-Hl | Mean YFT-Hl | Geom Mean |
|---|---|---|---|
| ① 293T-QD211-QP207208.... | 4381 | 7083 | 2063 |
| ② 293T-QD210-QP207208.... | 41.6 | 144 | 61.9 |
| ③ 293T-QD012-QP207208.... | 5.40 | 6.93 | 5.93 |
| ④ 293T-QD010-QP207208.... | 1.12E4 | 1.93E4 | 5712 |
| ⑤ 293T-QP207208.fcs | 25.9 | 34.9 | 31.5 |

Phage clone in 293T system
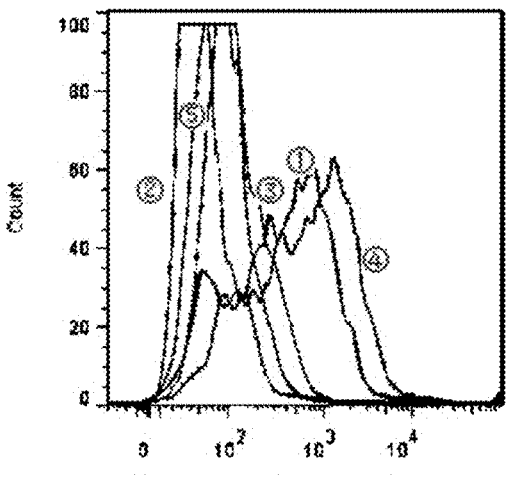
FIG. 6A
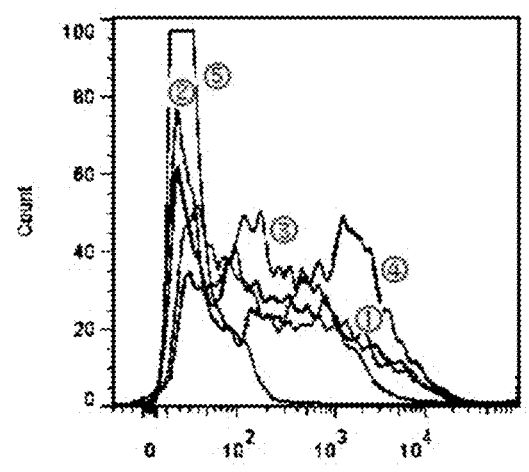
FIG. 6B
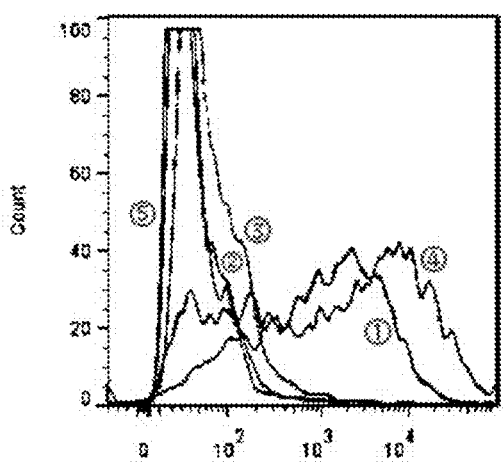
FIG. 6C
FIG. 6D

| Sample name | Media YFI-HI | Mean YFI-HI | Geom Mean |
|---|---|---|---|
| 293T-QD211-QP10911092... | 105 | 717 | 152 |
| 293T-QD210-QP10911092... | 28.6 | 49.6 | 28.9 |
| 293T-QD012-QP10911092... | 40.1 | 120 | 52.6 |
| 293T-QD010-QP10911092... | 307 | 1241 | 291 |
| 293T-QP10911092.fcs | 23.8 | 50.7 | 30.3 |

| Sample name | Media YFI-HI | Mean YFI-HI | Geom Mean |
|---|---|---|---|
| 293T-QD211-QP10991100... | 201 | 921 | 220 |
| 293T-QD210-QP10991100... | 30.5 | 78.7 | 28.2 |
| 293T-QD012-QP10991100... | 40.8 | 108 | 53.7 |
| 293T-QD010-QP10991100... | 830 | 1660 | 469 |
| 293T-QP10991100.fcs | 27.9 | 51.8 | 33.8 |

| Sample name | Media YFI-HI | Mean YFI-HI | Geom Mean |
|---|---|---|---|
| 293T-QD211-QP11031104... | 86.6 | 785 | 139 |
| 293T-QD210-QP11031104... | 28.0 | 164 | 46.4 |
| 293T-QD012-QP11031104... | 56.1 | 98.5 | 65.6 |
| 293T-QD010-QP11031104... | 230 | 1051 | 255 |
| 293T-QP11031104.fcs | 25.6 | 118 | 33.1 |

| Sample name | Media YFI-HI | Mean YFI-HI | Geom Mean |
|---|---|---|---|
| 293T-QD211-QP11051106... | 150 | 862 | 193 |
| 293T-QD210-QP11051106... | 24.2 | 66.7 | 34.4 |
| 293T-QD012-QP11051106... | 45.2 | 78.9 | 55.6 |
| 293T-QD010-QP11051106... | 5.31 | 5.95 | 5.69 |
| 293T-QP11071106.fcs | 31.1 | 58.7 | 36.9 |

Phage clone in 293T system

| Sample name | Media YFT-HI | Mean YFT-HI | Geom Mean |
|---|---|---|---|
| 293T-QD211-QP11071108... | 849 | 3153 | 863 |
| 293T-QD210-QP11071108... | 22.3 | 49.6 | 28.7 |
| 293T-QD012-QP11071108... | 42.8 | 72.8 | 53.5 |
| 293T-QD010-QP11071108... | 1265 | 5843 | 1196 |
| 293T-QP11071108.fcs | 31.1 | 58.7 | 36.9 |

| Sample name | Media YFT-HI | Mean YFT-HI | Geom Mean |
|---|---|---|---|
| 293T-QD211-QP11091110... | 1229 | 3872 | 885 |
| 293T-QD210-QP11091110... | 21.4 | 59.5 | 29.7 |
| 293T-QD012-QP11091110... | 40.4 | 71.3 | 51.2 |
| 293T-QD010-QP11091110... | 1447 | 6026 | 1374 |
| 293T-QP11091110.fcs | 24.8 | 38.7 | 31.1 |

| Sample name | Media YFT-HI | Mean YFT-HI | Geom Mean |
|---|---|---|---|
| 293T-QD211-QP11111112... | 709 | 2751 | 601 |
| 293T-QD210-QP11111112... | 19.9 | 36.5 | 28.3 |
| 293T-QD012-QP11111112... | 39.7 | 73.4 | 50.9 |
| 293T-QD010-QP11111112... | 1702 | 8425 | 1308 |
| 293T-QP11111112.fcs | 26.7 | 46.2 | 32.7 |

| Sample name | Media YFT-HI | Mean YFT-HI | Geom Mean |
|---|---|---|---|
| 293T-QD211-QP11131114... | 1806 | 3205 | 738 |
| 293T-QD210-QP11131114... | 30.5 | 92.6 | 31.3 |
| 293T-QD012-QP11131114... | 42.7 | 159 | 60.0 |
| 293T-QD010-QP11131114... | 2219 | 7160 | 1618 |
| 293T-QP11131114.fcs | 27.7 | 107 | 37.1 |

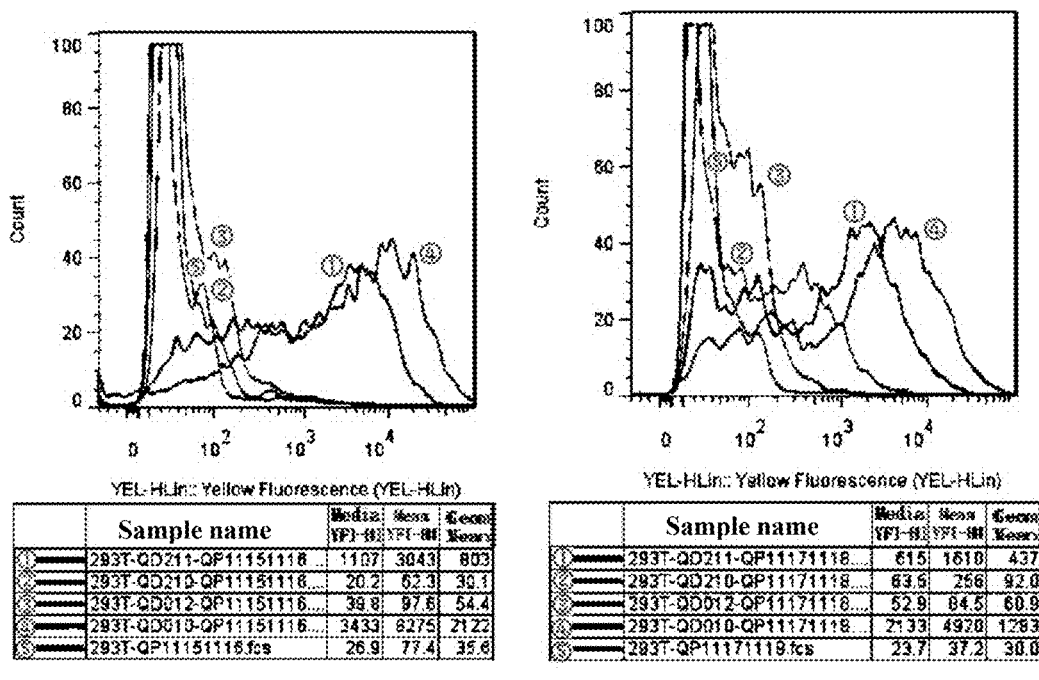
FIG. 7E                    FIG.7F
The binding ability of antibody to gastric cancer PDX model
GA0006 tumor cells
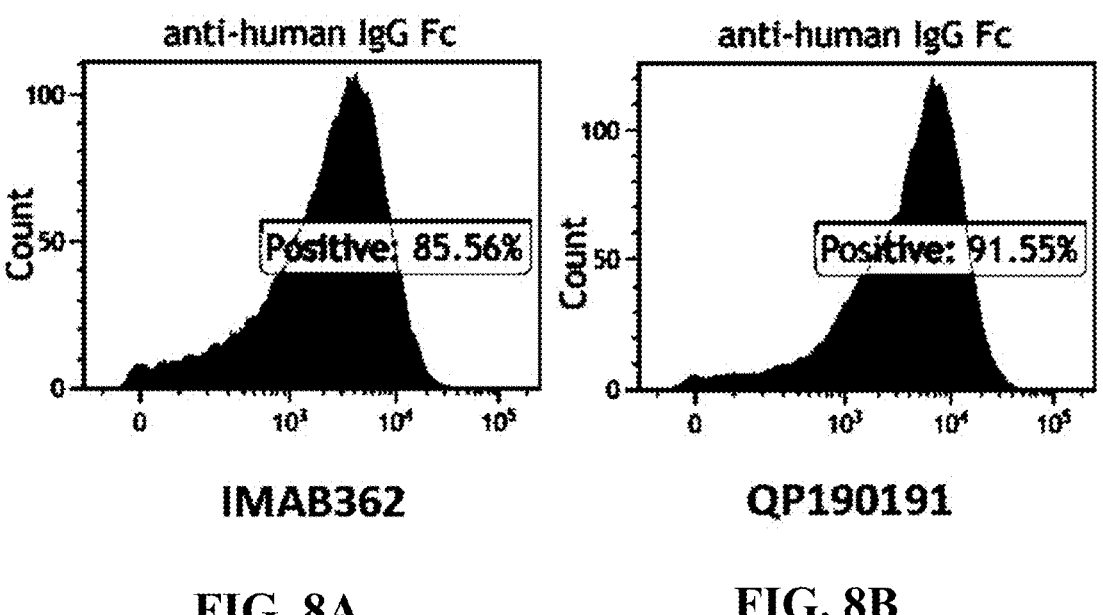
IMAB362                    QP190191
FIG. 8A                    FIG. 8B

QP192193

QP201202

QP207208

QP11091110

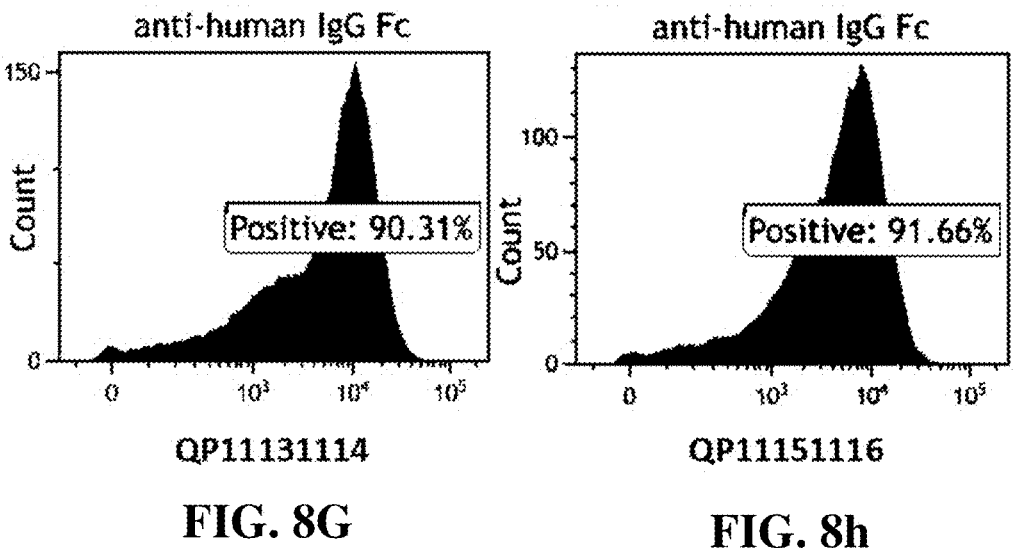
FIG. 8G                    FIG. 8h
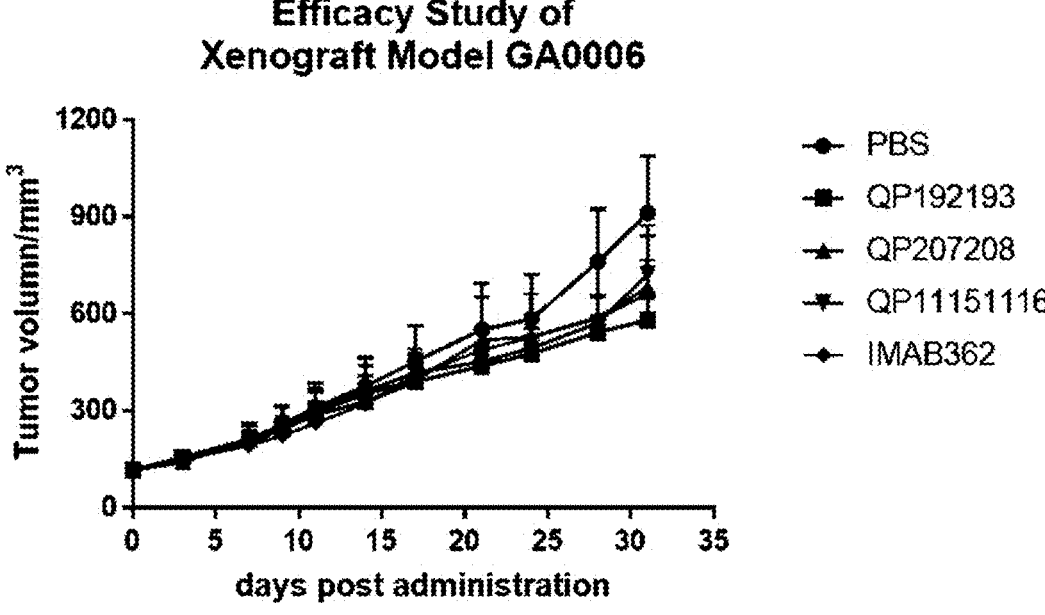
FIG. 9

PBS

QP192193

QP207208

QP11151116

PBS
BIW×8 i.p.

QP192193
10mpk BIW×8 i.p.

QP207208
10mpk BIW×8 i.p.

IMAB362
10mpk BIW×8 i.p.

QP11151116
10mpk BIW×8 i.p.

Body Weight

- PBS
- QP192193
- QP207208
- QP11151116
- IMAB362 body weight /g days post administration

SEQUENCE LISTING

<160> NUMBER OF SEQ ID NOS: 121

<210> SEQ ID NO 1
<211> LENGTH: 119
<212> TYPE: PRT
<213> ORGANISM: Artificial sequence
<220> FEATURE:
<223> OTHER INFORMATION: heavy chain variable region

<400> SEQUENCE: 1

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

```
Gly Ile Asn Trp Val Arg Gln Arg Pro Glu Gln Gly Leu Glu Trp Ile
        35                  40                  45

Gly Trp Leu Phe Pro Gly Asp Gly Thr Ile Lys Tyr Asn Glu Asn Phe
    50                  55                  60

Lys Gly Lys Ala Thr Leu Thr Thr Asp Arg Ser Ser Ser Ala Ala Tyr
65                  70                  75                  80

Met Gln Leu Ser Arg Leu Thr Ser Glu Asp Ser Ala Val Tyr Phe Cys
                85                  90                  95

Ala Arg Gly Gly Tyr Tyr Gly Asn Ala Met Asp Tyr Trp Gly Gln Gly
                100                 105                 110

Thr Ser Val Thr Val Ser Ser
        115
```

```
<210> SEQ ID NO 2
<211> LENGTH: 117
<212> TYPE: PRT
<213> ORGANISM: Artificial sequence
<220> FEATURE:
<223> OTHER INFORMATION: heavy chain variable region

<400> SEQUENCE: 2
```

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
        20                  25                  30

Ala Met Ser Trp Val Arg Gln Thr Pro Glu Lys Arg Leu Glu Trp Val
        35                  40                  45

Ala Ser Ile Ile Ser Gly Gly Arg Thr Tyr Tyr Leu Asp Ser Glu Lys
    50                  55                  60

Gly Arg Phe Thr Ile Ser Arg Asp Asn Ala Arg Asn Asn Leu Tyr Leu
65                  70                  75                  80

Gln Met Ser Ser Leu Arg Ser Glu Asp Thr Ala Met Tyr Tyr Cys Thr
                85                  90                  95

Arg Ile Tyr Tyr Gly Asn Ser Phe Asp Tyr Trp Gly Gln Gly Thr Thr
                100                 105                 110

Leu Thr Val Ser Ser
        115
```

```
<210> SEQ ID NO 3
<211> LENGTH: 118
<212> TYPE: PRT
<213> ORGANISM: Artificial sequence
<220> FEATURE:
<223> OTHER INFORMATION: heavy chain variable region

<400> SEQUENCE: 3
```

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
        20                  25                  30

Trp Met Asn Trp Val Lys Gln Arg Pro Gly Gln Gly Leu Glu Trp Ile
        35                  40                  45

Gly Gln Ile Tyr Pro Gly Asn Gly Asp Thr Thr Tyr Asn Gly Lys Phe
    50                  55                  60

Lys Gly Gln Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Phe Cys
```

-continued

```
                   85                    90                    95

Ala Arg Phe Val Lys Gly Asn Ala Met Asp Tyr Trp Gly Gln Gly Thr
               100                   105                   110

Ser Val Thr Val Ser Ser
        115

<210> SEQ ID NO 4
<211> LENGTH: 118
<212> TYPE: PRT
<213> ORGANISM: Artificial sequence
<220> FEATURE:
<223> OTHER INFORMATION: heavy chain variable region

<400> SEQUENCE: 4

Gln Val Gln Leu Gln Gln Ser Gly Ala Glu Leu Val Arg Pro Gly Ser
1                   5                    10                    15

Ser Val Lys Ile Ser Cys Lys Ala Ser Gly Tyr Ala Phe Ser Ser Tyr
               20                    25                    30

Trp Met Asn Trp Val Lys Gln Arg Pro Gly Gln Gly Leu Glu Trp Ile
           35                    40                    45

Gly Gln Ile Tyr Pro Gly Asn Gly Asp Thr Thr Tyr Asn Gly Lys Phe
       50                    55                    60

Lys Gly Gln Ala Thr Leu Thr Ala Asp Lys Ser Ser Ser Thr Val Tyr
65                    70                    75                    80

Met Gln Leu Ser Ser Leu Thr Ser Glu Asp Ser Ala Val Tyr Phe Cys
                   85                    90                    95

Ala Arg Phe Val Lys Gly Asn Ala Met Asp Tyr Trp Gly Gln Gly Thr
               100                   105                   110

Ser Val Thr Val Ser Ser
        115

<210> SEQ ID NO 5
<211> LENGTH: 119
<212> TYPE: PRT
<213> ORGANISM: Artificial sequence
<220> FEATURE:
<223> OTHER INFORMATION: heavy chain variable region

<400> SEQUENCE: 5

Asp Val Gln Leu Val Glu Ser Gly Gly Gly Leu Val Gln Pro Gly Gly
1                   5                    10                    15

Ser Arg Lys Leu Ser Cys Ala Ala Ser Gly Phe Thr Phe Ser Ser Phe
               20                    25                    30

Gly Met His Trp Val Arg Gln Ala Pro Glu Lys Gly Leu Glu Trp Val
           35                    40                    45

Ala Tyr Ile Ser Ser Gly Ser Asn Ser Ile Tyr Tyr Val Asp Thr Val
       50                    55                    60

Lys Gly Arg Phe Thr Ile Ser Arg Asp Asn Pro Lys Asn Thr Leu Phe
65                    70                    75                    80

Leu Gln Met Thr Ser Leu Lys Ser Glu Asp Thr Ala Met Tyr Tyr Cys
                   85                    90                    95

Ala Arg Asn Ala Tyr Tyr Gly Asn Ser Phe Asp Tyr Trp Gly Gln Gly
               100                   105                   110

Thr Thr Leu Thr Val Ser Ser
        115

<210> SEQ ID NO 6
<211> LENGTH: 115
```

<212> TYPE: PRT
<213> ORGANISM: Artificial sequence
<220> FEATURE:
<223> OTHER INFORMATION: heavy chain variable region

<400> SEQUENCE: 6

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Phe Val His Trp Val Lys Gln Lys Pro Gly Gln Gly Leu Glu Trp Ile
        35                  40                  45

Gly Tyr Ile Asn Pro Tyr Asn Asp Asp Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Leu Ser Leu Arg Phe Phe Ala Tyr Trp Gly Gln Gly Thr Leu Val Thr
            100                 105                 110

Val Ser Ala
        115

<210> SEQ ID NO 7
<211> LENGTH: 120
<212> TYPE: PRT
<213> ORGANISM: Artificial sequence
<220> FEATURE:
<223> OTHER INFORMATION: heavy chain variable region

<400> SEQUENCE: 7

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Val Tyr
65                  70                  75                  80

Met Glu Leu Ser Ser Leu Thr Ser Glu Asp Ser Ala Val Tyr Cys Cys
                85                  90                  95

Ala Arg Leu Gly Phe Thr Thr Arg Asn Ala Met Asp Tyr Trp Gly Gln
            100                 105                 110

Gly Thr Ser Val Thr Val Ser Ser
        115                 120

<210> SEQ ID NO 8
<211> LENGTH: 113
<212> TYPE: PRT
<213> ORGANISM: Artificial sequence
<220> FEATURE:
<223> OTHER INFORMATION: light chain variable region

<400> SEQUENCE: 8

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser

-continued

```
                20              25              30

Gly Asn Gln Lys Ser Tyr Leu Thr Trp Tyr Gln Gln Lys Pro Gly Gln
        35              40              45

Pro Pro Lys Leu Leu Ile Tyr Trp Ala Ser Thr Arg Glu Ser Gly Val
    50              55              60

Pro Asp Arg Phe Thr Gly Ser Gly Ser Gly Thr Asp Phe Thr Leu Thr
65              70              75              80

Ile Ser Ser Val Gln Ala Glu Asp Leu Ala Val Tyr Phe Cys Gln Asn
                85              90              95

Asp Tyr Phe Tyr Pro Tyr Thr Phe Gly Gly Gly Thr Lys Leu Glu Ile
            100             105             110

Lys

<210> SEQ ID NO 9
<211> LENGTH: 113
<212> TYPE: PRT
<213> ORGANISM: Artificial sequence
<220> FEATURE:
<223> OTHER INFORMATION: light chain variable region

<400> SEQUENCE: 9

Asp Ile Val Met Thr Gln Ser Pro Ser Ser Gln Thr Val Thr Ala Gly
1               5               10              15

Glu Lys Val Thr Met Ser Cys Lys Ser Ser Gln Ser Leu Leu Asn Ser
                20              25              30

Gly Asn Gln Lys Asn Tyr Leu Thr Trp Tyr Gln Gln Lys Pro Gly Gln
        35              40              45

Pro Pro Lys Leu Leu Ile Tyr Trp Ala Ser Thr Arg Glu Ser Gly Val
    50              55              60

Pro Asp Arg Phe Thr Gly Ser Gly Ser Gly Thr Asp Phe Thr Leu Thr
65              70              75              80

Ile Ser Asn Met Gln Ala Glu Asp Leu Ala Val Tyr Tyr Cys Gln Asn
                85              90              95

Asp Tyr Ser Tyr Pro Phe Thr Phe Gly Ser Gly Thr Lys Leu Glu Ile
            100             105             110

Lys

<210> SEQ ID NO 10
<211> LENGTH: 113
<212> TYPE: PRT
<213> ORGANISM: Artificial sequence
<220> FEATURE:
<223> OTHER INFORMATION: light chain variable region

<400> SEQUENCE: 10

Asp Ile Val Met Thr Gln Ser Pro Ser Ser Leu Thr Val Thr Ala Gly
1               5               10              15

Glu Lys Val Thr Met Ser Cys Lys Ser Ser Gln Ser Leu Leu Asn Ser
                20              25              30

Gly Asn Gln Lys Asn Tyr Leu Thr Trp Tyr Gln Gln Asn Pro Gly Gln
        35              40              45

Pro Pro Lys Met Leu Ile Tyr Trp Ala Ser Thr Arg Glu Ser Gly Val
    50              55              60

Pro Asp Arg Phe Thr Gly Ser Gly Ser Gly Ile Asp Phe Ser Leu Thr
65              70              75              80

Ile Ser Ser Val Gln Ala Glu Asp Leu Ala Leu Tyr Tyr Cys Gln Asn
                85              90              95
```

Ala Tyr Ser Tyr Pro Phe Thr Phe Gly Ser Gly Thr Lys Leu Glu Ile
                100                 105                 110

Lys

<210> SEQ ID NO 11
<211> LENGTH: 113
<212> TYPE: PRT
<213> ORGANISM: Artificial sequence
<220> FEATURE:
<223> OTHER INFORMATION: light chain variable region

<400> SEQUENCE: 11

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Arg Ala Glu Asp Leu Ala Val Tyr Tyr Cys Gln Asn
                85                  90                  95

Asp His Tyr Tyr Pro Phe Thr Phe Gly Ser Gly Thr Lys Leu Glu Ile
                100                 105                 110

Lys

<210> SEQ ID NO 12
<211> LENGTH: 113
<212> TYPE: PRT
<213> ORGANISM: Artificial sequence
<220> FEATURE:
<223> OTHER INFORMATION: light chain variable region

<400> SEQUENCE: 12

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Val Phe Thr Leu Thr
65                  70                  75                  80

Ile Ser Ser Val Gln Ala Glu Asp Leu Ala Val Tyr Phe Cys Gln Asn
                85                  90                  95

Asn Tyr Tyr Tyr Pro Leu Thr Phe Gly Ala Gly Thr Lys Leu Glu Leu
                100                 105                 110

Lys

<210> SEQ ID NO 13
<211> LENGTH: 113
<212> TYPE: PRT
<213> ORGANISM: Artificial sequence
<220> FEATURE:
<223> OTHER INFORMATION: light chain variable region -continued

<400> SEQUENCE: 13

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Ala Pro Lys Leu Leu Ile Tyr Trp Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser His Val Gln Ala Glu Asp Leu Ala Val Tyr Phe Cys Gln Asn
                85                  90                  95

Asp Tyr Ser Tyr Pro Leu Thr Phe Gly Ala Gly Thr Asn Leu Glu Leu
            100                 105                 110

Lys
```

<210> SEQ ID NO 14
<211> LENGTH: 113
<212> TYPE: PRT
<213> ORGANISM: Artificial sequence
<220> FEATURE:
<223> OTHER INFORMATION: light chain variable region

<400> SEQUENCE: 14

```
Asp Ile Val Met Thr Gln Ser Pro Ser Ser Leu Ser Val Ser Ala Gly
1               5                   10                  15

Glu Lys Val Thr Met Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Phe Thr Phe Gly Ser Gly Thr Lys Leu Glu Ile
            100                 105                 110

Lys
```

<210> SEQ ID NO 15
<211> LENGTH: 118
<212> TYPE: PRT
<213> ORGANISM: Artificial sequence
<220> FEATURE:
<223> OTHER INFORMATION: heavy chain variable region

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
```

```
          50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Ala Arg Asp Tyr Ala Phe Thr Gly Phe Asp Tyr Trp Gly Gln Gly Thr
                    100                 105                 110

Leu Val Thr Val Ser Ser
          115
```

<210> SEQ ID NO 16
<211> LENGTH: 120
<212> TYPE: PRT
<213> ORGANISM: Artificial sequence
<220> FEATURE:
<223> OTHER INFORMATION: heavy chain variable region

<400> SEQUENCE: 16

```
Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Ser Tyr
                    20                  25                  30

Tyr Met His Trp Val Arg Gln Ala Pro Gly Gln Gly Leu Glu Trp Met
          35                  40                  45

Gly Ile Ile Asn Pro Ser Gly Gly Ser Thr Ser Tyr Ala Gln Lys Phe
          50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Ala Arg Ser Ser Ala Tyr Gly Thr Tyr Ser Met Asp Tyr Trp Gly Gln
                    100                 105                 110

Gly Thr Leu Val Thr Val Ser Ser
          115                 120
```

<210> SEQ ID NO 17
<211> LENGTH: 121
<212> TYPE: PRT
<213> ORGANISM: Artificial sequence
<220> FEATURE:
<223> OTHER INFORMATION: heavy chain variable region

<400> SEQUENCE: 17

```
Gln Val Gln Leu Val Gln Ser Gly Ala Glu Val Lys Lys Pro Gly Ser
1                   5                   10                  15

Ser Val Lys Val Ser Cys Lys Ala Ser Gly Gly Thr Phe Ser Ser Tyr
                    20                  25                  30

Ala Ile Ser Trp Val Arg Gln Ala Pro Gly Gln Gly Leu Glu Trp Met
          35                  40                  45

Gly Gly Ile Ile Pro Ile Phe Gly Thr Ala Asn Tyr Ala Gln Lys Phe
          50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Gly Val Tyr Tyr Cys
                    85                  90                  95

Ala Arg Gly Ser Gly Ser Trp Phe Gly Pro Tyr Phe Asp Tyr Trp Gly
          100                 105                 110
```

-continued

```
Gln Gly Thr Thr Val Thr Val Ser Ser
        115                 120

<210> SEQ ID NO 18
<211> LENGTH: 118
<212> TYPE: PRT
<213> ORGANISM: Artificial sequence
<220> FEATURE:
<223> OTHER INFORMATION: heavy chain variable region

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Asp Gly Ala Thr Pro Phe Asp Tyr Trp Gly Gln Gly Thr
            100                 105                 110

Thr Val Thr Val Ser Ser
        115

<210> SEQ ID NO 19
<211> LENGTH: 120
<212> TYPE: PRT
<213> ORGANISM: Artificial sequence
<220> FEATURE:
<223> OTHER INFORMATION: heavy chain variable region

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ser Tyr Tyr Gly Thr Gly Ala Phe Asp Tyr Trp Gly Gln
            100                 105                 110

Gly Thr Thr Val Thr Val Ser Ser
        115                 120

<210> SEQ ID NO 20
<211> LENGTH: 121
<212> TYPE: PRT
<213> ORGANISM: Artificial sequence
<220> FEATURE:
<223> OTHER INFORMATION: heavy chain variable region
```

```
<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Gly Tyr Phe Ser Gly Leu Ala Phe Asp Tyr Trp Gly
            100                 105                 110

Gln Gly Thr Thr Val Thr Val Ser Ser
        115                 120

<210> SEQ ID NO 21
<211> LENGTH: 119
<212> TYPE: PRT
<213> ORGANISM: Artificial sequence
<220> FEATURE:
<223> OTHER INFORMATION: heavy chain variable region

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Asn Trp Ser Phe Gly Met Asp Tyr Trp Gly Gln Gly
            100                 105                 110

Thr Thr Val Thr Val Ser Ser
        115

<210> SEQ ID NO 22
<211> LENGTH: 119
<212> TYPE: PRT
<213> ORGANISM: Artificial sequence
<220> FEATURE:
<223> OTHER INFORMATION: heavy chain variable region

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45
```

```
Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Tyr Phe Pro Arg Ser Leu Asp Tyr Trp Gly Gln Gly
            100                 105                 110

Thr Thr Val Thr Val Ser Ser
        115

<210> SEQ ID NO 23
<211> LENGTH: 121
<212> TYPE: PRT
<213> ORGANISM: Artificial sequence
<220> FEATURE:
<223> OTHER INFORMATION: heavy chain variable region

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Trp Tyr Trp Leu Phe Gly Phe Asp Tyr Trp Gly
            100                 105                 110

Gln Gly Thr Thr Val Thr Val Ser Ser
        115                 120

<210> SEQ ID NO 24
<211> LENGTH: 119
<212> TYPE: PRT
<213> ORGANISM: Artificial sequence
<220> FEATURE:
<223> OTHER INFORMATION: heavy chain variable region

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Trp Gly Gly Tyr Met Asp Tyr Trp Gly Gln Gly
            100                 105                 110
```

-continued

```
Thr Thr Val Thr Val Ser Ser
        115

<210> SEQ ID NO 25
<211> LENGTH: 119
<212> TYPE: PRT
<213> ORGANISM: Artificial sequence
<220> FEATURE:
<223> OTHER INFORMATION: heavy chain variable region

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Tyr Tyr Phe Trp Phe Asp Tyr Trp Gly Gln Gly
            100                 105                 110

Thr Leu Val Thr Val Ser Ser
        115

<210> SEQ ID NO 26
<211> LENGTH: 119
<212> TYPE: PRT
<213> ORGANISM: Artificial sequence
<220> FEATURE:
<223> OTHER INFORMATION: heavy chain variable region

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Tyr Tyr Tyr Trp Phe Asp Tyr Trp Gly Gln Gly
            100                 105                 110

Thr Leu Val Thr Val Ser Ser
        115

<210> SEQ ID NO 27
<211> LENGTH: 119
<212> TYPE: PRT
<213> ORGANISM: Artificial sequence
<220> FEATURE:
<223> OTHER INFORMATION: heavy chain variable region
```

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Tyr Tyr Tyr Phe Trp Phe Asp Tyr Trp Gly Gln Gly
            100                 105                 110

Thr Leu Val Thr Val Ser Ser
            115
```

<210> SEQ ID NO 28
<211> LENGTH: 120
<212> TYPE: PRT
<213> ORGANISM: Artificial sequence
<220> FEATURE:
<223> OTHER INFORMATION: heavy chain variable region

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Tyr Tyr Tyr Phe Trp Phe Asp Tyr Trp Gly Gln
            100                 105                 110

Gly Thr Leu Val Thr Val Ser Ser
        115                 120
```

<210> SEQ ID NO 29
<211> LENGTH: 120
<212> TYPE: PRT
<213> ORGANISM: Artificial sequence
<220> FEATURE:
<223> OTHER INFORMATION: heavy chain variable region

<400> SEQUENCE: 29

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Asp Ser Tyr Tyr Tyr Phe Trp Tyr Asp Tyr Trp Gly Gln
            100             105             110

Gly Thr Leu Val Thr Val Ser Ser
        115             120
```

<210> SEQ ID NO 30
<211> LENGTH: 118
<212> TYPE: PRT
<213> ORGANISM: Artificial sequence
<220> FEATURE:
<223> OTHER INFORMATION: heavy chain variable region

<400> SEQUENCE: 30

```
Glu Val Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
            20              25              30

Ala Met Ser Trp Val Arg Gln Ala Pro Gly Lys Gly Leu Glu Trp Val
        35              40              45

Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Ala Ile Asp Tyr Tyr Thr Phe Asp Tyr Trp Gly Gln Gly Thr
            100             105             110

Leu Val Thr Val Ser Ser
        115
```

<210> SEQ ID NO 31
<211> LENGTH: 111
<212> TYPE: PRT
<213> ORGANISM: Artificial sequence
<220> FEATURE:
<223> OTHER INFORMATION: light chain variable region

<400> SEQUENCE: 31

```
Asp Ile Val Met Thr Gln Ser Pro Leu Ser Leu Pro Val Thr Pro Gly
1               5               10              15

Glu Pro Ala Ser Ile Ser Cys Arg Ser Ser Gln Ser Leu Leu His Ser
            20              25              30

Asn Gly Tyr Asn Tyr Leu Asp Trp Tyr Leu Gln Lys Pro Gly Gln Ser
        35              40              45

Pro Gln Leu Leu Ile Tyr Leu Gly Ser Asn Arg Ala Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Met Gln Ala
                85              90              95

Leu Met Thr Pro Thr Phe Gly Gln Gly Thr Lys Val Glu Ile Lys
```

-continued

```
                    100                 105                 110

<210> SEQ ID NO 32
<211> LENGTH: 111
<212> TYPE: PRT
<213> ORGANISM: Artificial sequence
<220> FEATURE:
<223> OTHER INFORMATION: light chain variable region

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Asp
                85                  90                  95

Leu Trp Pro Arg Thr Phe Gly Gln Gly Thr Lys Val Glu Ile Lys
            100                 105                 110

<210> SEQ ID NO 33
<211> LENGTH: 111
<212> TYPE: PRT
<213> ORGANISM: Artificial sequence
<220> FEATURE:
<223> OTHER INFORMATION: light chain variable region

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ala Gln Ser Pro Thr Phe Gly Gln Gly Thr Lys Val Glu Ile Lys
            100                 105                 110

<210> SEQ ID NO 34
<211> LENGTH: 112
<212> TYPE: PRT
<213> ORGANISM: Artificial sequence
<220> FEATURE:
<223> OTHER INFORMATION: light chain variable region

<400> SEQUENCE: 34

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Asn Thr Pro Pro Thr Phe Gly Gln Gly Thr Lys Val Glu Ile Lys
            100                 105                 110

<210> SEQ ID NO 35
<211> LENGTH: 111
<212> TYPE: PRT
<213> ORGANISM: Artificial sequence
<220> FEATURE:
<223> OTHER INFORMATION: light chain variable region

<400> SEQUENCE: 35

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Thr
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Met Thr Pro Thr Phe Gly Gln Gly Thr Lys Val Glu Ile Lys
            100                 105                 110

<210> SEQ ID NO 36
<211> LENGTH: 111
<212> TYPE: PRT
<213> ORGANISM: Artificial sequence
<220> FEATURE:
<223> OTHER INFORMATION: light chain variable region

<400> SEQUENCE: 36

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Arg Gln Phe Pro Thr Phe Gly Gln Gly Thr Lys Val Glu Ile Lys
            100                 105                 110
```

```
<210> SEQ ID NO 37
<211> LENGTH: 111
<212> TYPE: PRT
<213> ORGANISM: Artificial sequence
<220> FEATURE:
<223> OTHER INFORMATION: light chain variable region

<400> SEQUENCE: 37

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Asn Thr Phe Thr Phe Gly Gln Gly Thr Lys Val Glu Ile Lys
            100                 105                 110

<210> SEQ ID NO 38
<211> LENGTH: 111
<212> TYPE: PRT
<213> ORGANISM: Artificial sequence
<220> FEATURE:
<223> OTHER INFORMATION: light chain variable region

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Trp Asp Thr Phe Gly Gln Gly Thr Lys Val Glu Ile Lys
            100                 105                 110

<210> SEQ ID NO 39
<211> LENGTH: 111
<212> TYPE: PRT
<213> ORGANISM: Artificial sequence
<220> FEATURE:
<223> OTHER INFORMATION: light chain variable region

<400> SEQUENCE: 39

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45
```

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Gly Thr Phe Gly Gln Gly Thr Lys Val Glu Ile Lys
            100                 105                 110

<210> SEQ ID NO 40
<211> LENGTH: 113
<212> TYPE: PRT
<213> ORGANISM: Artificial sequence
<220> FEATURE:
<223> OTHER INFORMATION: light chain variable region

<400> SEQUENCE: 40

Asp Ile Val Met Thr Gln Ser Pro Asp Ser Leu Ala Val Ser Leu Gly
1                   5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Phe Thr Phe Gly Gln Gly Thr Lys Val Glu Ile
            100                 105                 110

Lys

<210> SEQ ID NO 41
<211> LENGTH: 106
<212> TYPE: PRT
<213> ORGANISM: Artificial sequence
<220> FEATURE:
<223> OTHER INFORMATION: light chain variable region

<400> SEQUENCE: 41

Asp Ile Gln Met Thr Gln Ser Pro Ser Thr Leu Ser Ala Ser Val Gly
1                   5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Gln Gly Thr Lys Val Glu Ile Lys
            100                 105

<210> SEQ ID NO 42

```
<211> LENGTH: 107
<212> TYPE: PRT
<213> ORGANISM: Artificial sequence
<220> FEATURE:
<223> OTHER INFORMATION: light chain variable region

<400> SEQUENCE: 42

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Tyr Ser Pro
                85                  90                  95

Thr Phe Gly Gln Gly Thr Lys Val Glu Ile Lys
            100                 105

<210> SEQ ID NO 43
<211> LENGTH: 107
<212> TYPE: PRT
<213> ORGANISM: Artificial sequence
<220> FEATURE:
<223> OTHER INFORMATION: light chain variable region

<400> SEQUENCE: 43

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Lys Phe Thr Leu Thr Ile Ser Ser Leu Gln Pro
65                  70                  75                  80

Asp Asp Phe Ala Thr Tyr Tyr Cys Gln Gln Tyr Ser Thr Tyr Pro Leu
                85                  90                  95

Thr Phe Gly Gln Gly Thr Lys Val Glu Ile Lys
            100                 105

<210> SEQ ID NO 44
<211> LENGTH: 107
<212> TYPE: PRT
<213> ORGANISM: Artificial sequence
<220> FEATURE:
<223> OTHER INFORMATION: light chain variable region

<400> SEQUENCE: 44

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45
```

```
Tyr Asp Ala Ser Ser Leu Glu Ser Gly Val Pro Ser Arg Phe Ser Gly
    50              55                  60

Ser Gly Ser Gly Thr Glu Phe Thr Leu Thr Ile Ser Ser Leu Gln Pro
65              70                  75                  80

Asp Asp Phe Ala Thr Tyr Tyr Cys Gln Gln Tyr Leu Ser Tyr Pro Pro
                85                  90                  95

Thr Phe Gly Gln Gly Thr Lys Val Glu Ile Lys
            100                 105
```

<210> SEQ ID NO 45
<211> LENGTH: 107
<212> TYPE: PRT
<213> ORGANISM: Artificial sequence
<220> FEATURE:
<223> OTHER INFORMATION: light chain variable region

<400> SEQUENCE: 45

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50              55                  60

Ser Gly Ser Gly Thr Glu Phe Thr Leu Thr Ile Ser Ser Leu Gln Pro
65              70                  75                  80

Asp Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys
            100                 105
```

<210> SEQ ID NO 46
<211> LENGTH: 107
<212> TYPE: PRT
<213> ORGANISM: Artificial sequence
<220> FEATURE:
<223> OTHER INFORMATION: light chain variable region

<400> SEQUENCE: 46

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50              55                  60

Ser Gly Ser Gly Thr Glu Phe Thr Leu Thr Ile Ser Ser Leu Gln Pro
65              70                  75                  80

Asp Asp Phe Ala Thr Tyr Tyr Cys Gln Gln Tyr Ser Thr Tyr Pro Leu
                85                  90                  95

Thr Phe Gly Gln Gly Thr Lys Val Glu Val Lys
            100                 105
```

<210> SEQ ID NO 47
<211> LENGTH: 5
<212> TYPE: PRT
<213> ORGANISM: Artificial sequence -continued

```
<220> FEATURE:
<223> OTHER INFORMATION: CDR

<400> SEQUENCE: 47

Ser Tyr Ile Met His
1               5

<210> SEQ ID NO 48
<211> LENGTH: 17
<212> TYPE: PRT
<213> ORGANISM: Artificial sequence
<220> FEATURE:
<223> OTHER INFORMATION: CDR

<400> SEQUENCE: 48

Tyr Ile Asn Pro Tyr Asn Asp Gly Thr Lys Tyr Asn Glu Lys Phe Lys
1               5                   10                  15

Gly

<210> SEQ ID NO 49
<211> LENGTH: 11
<212> TYPE: PRT
<213> ORGANISM: Artificial sequence
<220> FEATURE:
<223> OTHER INFORMATION: CDR

<400> SEQUENCE: 49

Leu Gly Phe Thr Thr Arg Asn Ala Met Asp Tyr
1               5                   10

<210> SEQ ID NO 50
<211> LENGTH: 17
<212> TYPE: PRT
<213> ORGANISM: Artificial sequence
<220> FEATURE:
<223> OTHER INFORMATION: CDR

<400> SEQUENCE: 50

Lys Ser Ser Gln Ser Leu Leu Asn Ser Gly Asn Gln Lys Asn Tyr Leu
1               5                   10                  15

Ala

<210> SEQ ID NO 51
<211> LENGTH: 7
<212> TYPE: PRT
<213> ORGANISM: Artificial sequence
<220> FEATURE:
<223> OTHER INFORMATION: CDR

<400> SEQUENCE: 51

Gly Ala Ser Thr Arg Glu Ser
1               5

<210> SEQ ID NO 52
<211> LENGTH: 7
<212> TYPE: PRT
<213> ORGANISM: Artificial sequence
<220> FEATURE:
<223> OTHER INFORMATION: CDR

<400> SEQUENCE: 52

Gln Asn Asp His Ser Tyr Pro
1               5

<210> SEQ ID NO 53
```

```
<211> LENGTH: 5
<212> TYPE: PRT
<213> ORGANISM: Artificial sequence
<220> FEATURE:
<223> OTHER INFORMATION: CDR

<400> SEQUENCE: 53

Ser Tyr Gly Ile Asn
1               5

<210> SEQ ID NO 54
<211> LENGTH: 17
<212> TYPE: PRT
<213> ORGANISM: Artificial sequence
<220> FEATURE:
<223> OTHER INFORMATION: CDR

<400> SEQUENCE: 54

Trp Leu Phe Pro Gly Asp Gly Thr Ile Lys Tyr Asn Glu Asn Phe Lys
1               5                   10                  15

Gly

<210> SEQ ID NO 55
<211> LENGTH: 10
<212> TYPE: PRT
<213> ORGANISM: Artificial sequence
<220> FEATURE:
<223> OTHER INFORMATION: CDR

<400> SEQUENCE: 55

Gly Gly Tyr Tyr Gly Asn Ala Met Asp Tyr
1               5                   10

<210> SEQ ID NO 56
<211> LENGTH: 17
<212> TYPE: PRT
<213> ORGANISM: Artificial sequence
<220> FEATURE:
<223> OTHER INFORMATION: CDR

<400> SEQUENCE: 56

Lys Ser Ser Gln Ser Leu Leu Asn Ser Gly Asn Gln Lys Ser Tyr Leu
1               5                   10                  15

Thr

<210> SEQ ID NO 57
<211> LENGTH: 7
<212> TYPE: PRT
<213> ORGANISM: Artificial sequence
<220> FEATURE:
<223> OTHER INFORMATION: CDR

<400> SEQUENCE: 57

Trp Ala Ser Thr Arg Glu Ser
1               5

<210> SEQ ID NO 58
<211> LENGTH: 9
<212> TYPE: PRT
<213> ORGANISM: Artificial sequence
<220> FEATURE:
<223> OTHER INFORMATION: CDR

<400> SEQUENCE: 58

Gln Asn Asp Tyr Phe Tyr Pro Tyr Thr
1               5
```

<210> SEQ ID NO 59
<211> LENGTH: 5
<212> TYPE: PRT
<213> ORGANISM: Artificial sequence
<220> FEATURE:
<223> OTHER INFORMATION: CDR

<400> SEQUENCE: 59

Asn Tyr Ala Met Ser
1               5

<210> SEQ ID NO 60
<211> LENGTH: 16
<212> TYPE: PRT
<213> ORGANISM: Artificial sequence
<220> FEATURE:
<223> OTHER INFORMATION: CDR

<400> SEQUENCE: 60

Ser Ile Ile Ser Gly Gly Arg Thr Tyr Tyr Leu Asp Ser Glu Lys Gly
1               5                   10                  15

<210> SEQ ID NO 61
<211> LENGTH: 9
<212> TYPE: PRT
<213> ORGANISM: Artificial sequence
<220> FEATURE:
<223> OTHER INFORMATION: CDR

<400> SEQUENCE: 61

Ile Tyr Tyr Gly Asn Ser Phe Asp Tyr
1               5

<210> SEQ ID NO 62
<211> LENGTH: 17
<212> TYPE: PRT
<213> ORGANISM: Artificial sequence
<220> FEATURE:
<223> OTHER INFORMATION: CDR

<400> SEQUENCE: 62

Lys Ser Ser Gln Ser Leu Leu Asn Ser Gly Asn Gln Lys Asn Tyr Leu
1               5                   10                  15

Thr

<210> SEQ ID NO 63
<211> LENGTH: 9
<212> TYPE: PRT
<213> ORGANISM: Artificial sequence
<220> FEATURE:
<223> OTHER INFORMATION: CDR

<400> SEQUENCE: 63

Gln Asn Asp Tyr Ser Tyr Pro Phe Thr
1               5

<210> SEQ ID NO 64
<211> LENGTH: 5
<212> TYPE: PRT
<213> ORGANISM: Artificial sequence
<220> FEATURE:
<223> OTHER INFORMATION: CDR

<400> SEQUENCE: 64

Ser Tyr Trp Met Asn

-continued

```
1               5

<210> SEQ ID NO 65
<211> LENGTH: 17
<212> TYPE: PRT
<213> ORGANISM: Artificial sequence
<220> FEATURE:
<223> OTHER INFORMATION: CDR

<400> SEQUENCE: 65

Gln Ile Tyr Pro Gly Asn Gly Asp Thr Thr Tyr Asn Gly Lys Phe Lys
1               5                   10                  15

Gly

<210> SEQ ID NO 66
<211> LENGTH: 9
<212> TYPE: PRT
<213> ORGANISM: Artificial sequence
<220> FEATURE:
<223> OTHER INFORMATION: CDR

<400> SEQUENCE: 66

Phe Val Lys Gly Asn Ala Met Asp Tyr
1               5

<210> SEQ ID NO 67
<211> LENGTH: 9
<212> TYPE: PRT
<213> ORGANISM: Artificial sequence
<220> FEATURE:
<223> OTHER INFORMATION: CDR

<400> SEQUENCE: 67

Gln Asn Ala Tyr Ser Tyr Pro Phe Thr
1               5

<210> SEQ ID NO 68
<211> LENGTH: 5
<212> TYPE: PRT
<213> ORGANISM: Artificial sequence
<220> FEATURE:
<223> OTHER INFORMATION: CDR

<400> SEQUENCE: 68

Ile Tyr Gly Val His
1               5

<210> SEQ ID NO 69
<211> LENGTH: 16
<212> TYPE: PRT
<213> ORGANISM: Artificial sequence
<220> FEATURE:
<223> OTHER INFORMATION: CDR

<400> SEQUENCE: 69

Val Ile Trp Ala Gly Gly Ser Thr Asn Tyr Asn Ser Ala Leu Met Ser
1               5                   10                  15

<210> SEQ ID NO 70
<211> LENGTH: 10
<212> TYPE: PRT
<213> ORGANISM: Artificial sequence
<220> FEATURE:
<223> OTHER INFORMATION: CDR

<400> SEQUENCE: 70
```

-continued

```
Asp Tyr Tyr Tyr Gly Ser Gly Phe Asp Tyr
1               5                   10

<210> SEQ ID NO 71
<211> LENGTH: 9
<212> TYPE: PRT
<213> ORGANISM: Artificial sequence
<220> FEATURE:
<223> OTHER INFORMATION: CDR

<400> SEQUENCE: 71

Gln Asn Asp His Tyr Tyr Pro Phe Thr
1               5

<210> SEQ ID NO 72
<211> LENGTH: 5
<212> TYPE: PRT
<213> ORGANISM: Artificial sequence
<220> FEATURE:
<223> OTHER INFORMATION: CDR

<400> SEQUENCE: 72

Ser Phe Gly Met His
1               5

<210> SEQ ID NO 73
<211> LENGTH: 17
<212> TYPE: PRT
<213> ORGANISM: Artificial sequence
<220> FEATURE:
<223> OTHER INFORMATION: CDR

<400> SEQUENCE: 73

Tyr Ile Ser Ser Gly Ser Asn Ser Ile Tyr Tyr Val Asp Thr Val Lys
1               5                   10                  15

Gly

<210> SEQ ID NO 74
<211> LENGTH: 10
<212> TYPE: PRT
<213> ORGANISM: Artificial sequence
<220> FEATURE:
<223> OTHER INFORMATION: CDR

<400> SEQUENCE: 74

Asn Ala Tyr Tyr Gly Asn Ser Phe Asp Tyr
1               5                   10

<210> SEQ ID NO 75
<211> LENGTH: 9
<212> TYPE: PRT
<213> ORGANISM: Artificial sequence
<220> FEATURE:
<223> OTHER INFORMATION: CDR

<400> SEQUENCE: 75

Gln Asn Asn Tyr Tyr Tyr Pro Leu Thr
1               5

<210> SEQ ID NO 76
<211> LENGTH: 5
<212> TYPE: PRT
<213> ORGANISM: Artificial sequence
<220> FEATURE:
<223> OTHER INFORMATION: CDR

<400> SEQUENCE: 76
```

```
Asn Tyr Phe Val His
1               5

<210> SEQ ID NO 77
<211> LENGTH: 17
<212> TYPE: PRT
<213> ORGANISM: Artificial sequence
<220> FEATURE:
<223> OTHER INFORMATION: CDR

<400> SEQUENCE: 77

Tyr Ile Asn Pro Tyr Asn Asp Asp Thr Lys Tyr Asn Glu Lys Phe Lys
1               5                   10                  15

Gly

<210> SEQ ID NO 78
<211> LENGTH: 8
<212> TYPE: PRT
<213> ORGANISM: Artificial sequence
<220> FEATURE:
<223> OTHER INFORMATION: CDR

<400> SEQUENCE: 78

Leu Ser Leu Arg Phe Phe Ala Tyr
1               5

<210> SEQ ID NO 79
<211> LENGTH: 9
<212> TYPE: PRT
<213> ORGANISM: Artificial sequence
<220> FEATURE:
<223> OTHER INFORMATION: CDR

<400> SEQUENCE: 79

Gln Asn Asp Tyr Ser Tyr Pro Leu Thr
1               5

<210> SEQ ID NO 80
<211> LENGTH: 5
<212> TYPE: PRT
<213> ORGANISM: Artificial sequence
<220> FEATURE:
<223> OTHER INFORMATION: CDR

<400> SEQUENCE: 80

Ser Tyr Ala Met Ser
1               5

<210> SEQ ID NO 81
<211> LENGTH: 17
<212> TYPE: PRT
<213> ORGANISM: Artificial sequence
<220> FEATURE:
<223> OTHER INFORMATION: CDR

<400> SEQUENCE: 81

Ala Ile Ser Gly Ser Gly Gly Ser Thr Tyr Tyr Ala Asp Ser Val Lys
1               5                   10                  15

Gly

<210> SEQ ID NO 82
<211> LENGTH: 10
<212> TYPE: PRT
<213> ORGANISM: Artificial sequence
<220> FEATURE:
```

<223> OTHER INFORMATION: CDR

<400> SEQUENCE: 82

Asp Tyr Tyr Tyr Tyr Phe Trp Phe Asp Tyr
1               5                   10

<210> SEQ ID NO 83
<211> LENGTH: 11
<212> TYPE: PRT
<213> ORGANISM: Artificial sequence
<220> FEATURE:
<223> OTHER INFORMATION: CDR

<400> SEQUENCE: 83

Arg Ala Ser Gln Ser Ile Ser Ser Trp Leu Ala
1               5                   10

<210> SEQ ID NO 84
<211> LENGTH: 7
<212> TYPE: PRT
<213> ORGANISM: Artificial sequence
<220> FEATURE:
<223> OTHER INFORMATION: CDR

<400> SEQUENCE: 84

Asp Ala Ser Ser Leu Glu Ser
1               5

<210> SEQ ID NO 85
<211> LENGTH: 8
<212> TYPE: PRT
<213> ORGANISM: Artificial sequence
<220> FEATURE:
<223> OTHER INFORMATION: CDR

<400> SEQUENCE: 85

Gln Gln Tyr Asn Ser Tyr Ser Thr
1               5

<210> SEQ ID NO 86
<211> LENGTH: 10
<212> TYPE: PRT
<213> ORGANISM: Artificial sequence
<220> FEATURE:
<223> OTHER INFORMATION: CDR

<400> SEQUENCE: 86

Asp Tyr Tyr Tyr Tyr Tyr Trp Phe Asp Tyr
1               5                   10

<210> SEQ ID NO 87
<211> LENGTH: 9
<212> TYPE: PRT
<213> ORGANISM: Artificial sequence
<220> FEATURE:
<223> OTHER INFORMATION: CDR

<400> SEQUENCE: 87

Gln Gln Tyr Ser Ser Tyr Ser Pro Thr
1               5

<210> SEQ ID NO 88
<211> LENGTH: 10
<212> TYPE: PRT
<213> ORGANISM: Artificial sequence
<220> FEATURE:
<223> OTHER INFORMATION: CDR

<400> SEQUENCE: 88

Gly Tyr Tyr Tyr Tyr Phe Trp Phe Asp Tyr
1               5                   10

<210> SEQ ID NO 89
<211> LENGTH: 9
<212> TYPE: PRT
<213> ORGANISM: Artificial sequence
<220> FEATURE:
<223> OTHER INFORMATION: CDR

<400> SEQUENCE: 89

Gln Gln Tyr Ser Thr Tyr Pro Leu Thr
1               5

<210> SEQ ID NO 90
<211> LENGTH: 11
<212> TYPE: PRT
<213> ORGANISM: Artificial sequence
<220> FEATURE:
<223> OTHER INFORMATION: CDR

<400> SEQUENCE: 90

Ser Ala Ala Tyr Tyr Tyr Phe Trp Phe Asp Tyr
1               5                   10

<210> SEQ ID NO 91
<211> LENGTH: 9
<212> TYPE: PRT
<213> ORGANISM: Artificial sequence
<220> FEATURE:
<223> OTHER INFORMATION: CDR

<400> SEQUENCE: 91

Gln Gln Tyr Leu Ser Tyr Pro Pro Thr
1               5

<210> SEQ ID NO 92
<211> LENGTH: 11
<212> TYPE: PRT
<213> ORGANISM: Artificial sequence
<220> FEATURE:
<223> OTHER INFORMATION: CDR

<400> SEQUENCE: 92

Asp Ser Tyr Tyr Tyr Tyr Phe Trp Tyr Asp Tyr
1               5                   10

<210> SEQ ID NO 93
<211> LENGTH: 9
<212> TYPE: PRT
<213> ORGANISM: Artificial sequence
<220> FEATURE:
<223> OTHER INFORMATION: CDR

<400> SEQUENCE: 93

Gln Gln Tyr Asn Ser Tyr Pro Leu Thr
1               5

<210> SEQ ID NO 94
<211> LENGTH: 9
<212> TYPE: PRT
<213> ORGANISM: Artificial sequence
<220> FEATURE:
<223> OTHER INFORMATION: CDR

<400> SEQUENCE: 94

Ala Ile Asp Tyr Tyr Thr Phe Asp Tyr
1               5

<210> SEQ ID NO 95
<211> LENGTH: 9
<212> TYPE: PRT
<213> ORGANISM: Artificial sequence
<220> FEATURE:
<223> OTHER INFORMATION: CDR

<400> SEQUENCE: 95

Gln Gln Tyr Ser Thr Tyr Pro Leu Thr
1               5

<210> SEQ ID NO 96
<211> LENGTH: 5
<212> TYPE: PRT
<213> ORGANISM: Artificial sequence
<220> FEATURE:
<223> OTHER INFORMATION: CDR

<400> SEQUENCE: 96

Ser Tyr Tyr Met His
1               5

<210> SEQ ID NO 97
<211> LENGTH: 17
<212> TYPE: PRT
<213> ORGANISM: Artificial sequence
<220> FEATURE:
<223> OTHER INFORMATION: CDR

<400> SEQUENCE: 97

Ile Ile Asn Pro Ser Gly Gly Ser Thr Ser Tyr Ala Gln Lys Phe Gln
1               5                   10                  15

Gly

<210> SEQ ID NO 98
<211> LENGTH: 9
<212> TYPE: PRT
<213> ORGANISM: Artificial sequence
<220> FEATURE:
<223> OTHER INFORMATION: CDR

<400> SEQUENCE: 98

Asp Tyr Ala Phe Thr Gly Phe Asp Tyr
1               5

<210> SEQ ID NO 99
<211> LENGTH: 16
<212> TYPE: PRT
<213> ORGANISM: Artificial sequence
<220> FEATURE:
<223> OTHER INFORMATION: CDR

<400> SEQUENCE: 99

Arg Ser Ser Gln Ser Leu Leu His Ser Asn Gly Tyr Asn Tyr Leu Asp
1               5                   10                  15

<210> SEQ ID NO 100
<211> LENGTH: 7
<212> TYPE: PRT
<213> ORGANISM: Artificial sequence
<220> FEATURE:
<223> OTHER INFORMATION: CDR

<400> SEQUENCE: 100

Leu Gly Ser Asn Arg Ala Ser
1               5

<210> SEQ ID NO 101
<211> LENGTH: 8
<212> TYPE: PRT
<213> ORGANISM: Artificial sequence
<220> FEATURE:
<223> OTHER INFORMATION: CDR

<400> SEQUENCE: 101

Met Gln Ala Leu Met Thr Pro Thr
1               5

<210> SEQ ID NO 102
<211> LENGTH: 11
<212> TYPE: PRT
<213> ORGANISM: Artificial sequence
<220> FEATURE:
<223> OTHER INFORMATION: CDR

<400> SEQUENCE: 102

Ser Ser Ala Tyr Gly Thr Tyr Ser Met Asp Tyr
1               5                   10

<210> SEQ ID NO 103
<211> LENGTH: 8
<212> TYPE: PRT
<213> ORGANISM: Artificial sequence
<220> FEATURE:
<223> OTHER INFORMATION: CDR

<400> SEQUENCE: 103

Met Gln Asp Leu Trp Pro Arg Thr
1               5

<210> SEQ ID NO 104
<211> LENGTH: 5
<212> TYPE: PRT
<213> ORGANISM: Artificial sequence
<220> FEATURE:
<223> OTHER INFORMATION: CDR

<400> SEQUENCE: 104

Ser Tyr Ala Ile Ser
1               5

<210> SEQ ID NO 105
<211> LENGTH: 17
<212> TYPE: PRT
<213> ORGANISM: Artificial sequence
<220> FEATURE:
<223> OTHER INFORMATION: CDR

<400> SEQUENCE: 105

Gly Ile Ile Pro Ile Phe Gly Thr Ala Asn Tyr Ala Gln Lys Phe Gln
1               5                   10                  15

Gly

<210> SEQ ID NO 106
<211> LENGTH: 12
<212> TYPE: PRT
<213> ORGANISM: Artificial sequence
<220> FEATURE:

<223> OTHER INFORMATION: CDR

<400> SEQUENCE: 106

Gly Ser Gly Ser Trp Phe Gly Pro Tyr Phe Asp Tyr
1               5                   10

<210> SEQ ID NO 107
<211> LENGTH: 8
<212> TYPE: PRT
<213> ORGANISM: Artificial sequence
<220> FEATURE:
<223> OTHER INFORMATION: CDR

<400> SEQUENCE: 107

Met Gln Ala Ala Gln Ser Pro Thr
1               5

<210> SEQ ID NO 108
<211> LENGTH: 9
<212> TYPE: PRT
<213> ORGANISM: Artificial sequence
<220> FEATURE:
<223> OTHER INFORMATION: CDR

<400> SEQUENCE: 108

Thr Asp Gly Ala Thr Pro Phe Asp Tyr
1               5

<210> SEQ ID NO 109
<211> LENGTH: 9
<212> TYPE: PRT
<213> ORGANISM: Artificial sequence
<220> FEATURE:
<223> OTHER INFORMATION: CDR

<400> SEQUENCE: 109

Met Gln Ala Leu Asn Thr Pro Pro Thr
1               5

<210> SEQ ID NO 110
<211> LENGTH: 11
<212> TYPE: PRT
<213> ORGANISM: Artificial sequence
<220> FEATURE:
<223> OTHER INFORMATION: CDR

<400> SEQUENCE: 110

Arg Ser Tyr Tyr Gly Thr Gly Ala Phe Asp Tyr
1               5                   10

<210> SEQ ID NO 111
<211> LENGTH: 12
<212> TYPE: PRT
<213> ORGANISM: Artificial sequence
<220> FEATURE:
<223> OTHER INFORMATION: CDR

<400> SEQUENCE: 111

Ser Leu Gly Tyr Phe Ser Gly Leu Ala Phe Asp Tyr
1               5                   10

<210> SEQ ID NO 112
<211> LENGTH: 8
<212> TYPE: PRT
<213> ORGANISM: Artificial sequence
<220> FEATURE:
<223> OTHER INFORMATION: CDR

<400> SEQUENCE: 112

Met Gln Gly Arg Gln Phe Pro Thr
1               5

<210> SEQ ID NO 113
<211> LENGTH: 10
<212> TYPE: PRT
<213> ORGANISM: Artificial sequence
<220> FEATURE:
<223> OTHER INFORMATION: CDR

<400> SEQUENCE: 113

Gly Tyr Asn Trp Ser Phe Gly Met Asp Tyr
1               5                   10

<210> SEQ ID NO 114
<211> LENGTH: 8
<212> TYPE: PRT
<213> ORGANISM: Artificial sequence
<220> FEATURE:
<223> OTHER INFORMATION: CDR

<400> SEQUENCE: 114

Met Gln Gly Leu Asn Thr Phe Thr
1               5

<210> SEQ ID NO 115
<211> LENGTH: 10
<212> TYPE: PRT
<213> ORGANISM: Artificial sequence
<220> FEATURE:
<223> OTHER INFORMATION: CDR

<400> SEQUENCE: 115

Ala Gly Tyr Phe Pro Arg Ser Leu Asp Tyr
1               5                   10

<210> SEQ ID NO 116
<211> LENGTH: 8
<212> TYPE: PRT
<213> ORGANISM: Artificial sequence
<220> FEATURE:
<223> OTHER INFORMATION: CDR

<400> SEQUENCE: 116

Met Gln Ala Leu Gln Trp Asp Thr
1               5

<210> SEQ ID NO 117
<211> LENGTH: 12
<212> TYPE: PRT
<213> ORGANISM: Artificial sequence
<220> FEATURE:
<223> OTHER INFORMATION: CDR

<400> SEQUENCE: 117

Gly Tyr Ser Trp Tyr Trp Leu Phe Gly Phe Asp Tyr
1               5                   10

<210> SEQ ID NO 118
<211> LENGTH: 8
<212> TYPE: PRT
<213> ORGANISM: Artificial sequence
<220> FEATURE:
<223> OTHER INFORMATION: CDR -continued

```
<400> SEQUENCE: 118

Met Gln Ala Leu Gln Thr Gly Thr
1               5

<210> SEQ ID NO 119
<211> LENGTH: 10
<212> TYPE: PRT
<213> ORGANISM: Artificial sequence
<220> FEATURE:
<223> OTHER INFORMATION: CDR

<400> SEQUENCE: 119

Gly Gly Asp Trp Gly Gly Tyr Met Asp Tyr
1               5                   10

<210> SEQ ID NO 120
<211> LENGTH: 17
<212> TYPE: PRT
<213> ORGANISM: Artificial sequence
<220> FEATURE:
<223> OTHER INFORMATION: CDR

<400> SEQUENCE: 120

Lys Ser Ser Gln Ser Val Leu Tyr Ser Ser Asn Asn Lys Asn Tyr Leu
1               5                   10                  15

Ala

<210> SEQ ID NO 121
<211> LENGTH: 9
<212> TYPE: PRT
<213> ORGANISM: Artificial sequence
<220> FEATURE:
<223> OTHER INFORMATION: CDR

<400> SEQUENCE: 121

Gln Gln Tyr Tyr Thr Thr Pro Phe Thr
1               5
```

ANTI-CLDN ANTIBODY AND PHARMACEUTICAL COMPOSITION THEREOF AND DETECTION METHOD THEREFOR

TECHNICAL FIELD

The present invention relates to an anti-CLDN antibody, the present invention also relates to a pharmaceutical composition comprising the anti-CLDN antibody, and the present invention also relates to a method for detecting whether CLDN is present in a biological sample.

BACKGROUND

Tight junction (TJ) plays a key role in the material flow between cells, maintains cell polarity by blocking the radial diffusion of membrane proteins and membrane lipids. In addition, it also participates in recruiting signal molecules that regulate cell proliferation, differentiation and movement. Tight junction is formed by claudin (CLDN), and the claudin family consists of more than 20 protein molecules, all of which contain a quadruple transmembrane domain and similar amino acid sequences, but their tissue distribution is specific. Human CLDN genes are distributed in pairs on different chromosomes, which implies that some CLDN genes are derived from gene replication.

The molecular weight of CLDN protein is mostly in the range of 20-34 kDa, and the biggest difference is the sequence and size of intracellular C-terminal, which contains a PDZ domain binding motif, which enables CLDN protein to directly interact with tight junction related proteins in cytoplasm, such as ZO-1, ZO-2, ZO-3 and MUPP1. In addition, this sequence contains post-transcriptional modification sites such as phosphorylation sites, which can affect the localization and function of protein molecules. MAPK (Mitogen-activated protein kinase) or PKC (protein kinase C) can phosphorylate CLDN1, and cAMP (cyclic AMP) can induce the phosphorylation of CLDN5, all of which can promote the barrier function of CLDN protein, while PKA-mediated phosphorylation of CLDN16 can enhance magnesium ion transport.

CLDN plays a key role in regulating selective permeation of cell bypass. CLDN2 and CLDN15 participate in the formation of cation channels and cation pores, while CLDN4/7/10 participate in the formation of anion channels and pores. Claudin protein is highly expressed in some cell lines, which affects transepithelial electrical resistance and permeability. In cultured epidermal-derived cells, CLDN1/4/5/7 can increase transepithelial electrical resistance, while CLDN2 and CLDN10 do not.

CLDN gene mutation is deemed relevant to various diseases. CLDN1 mutation may lead to sclerosing cholangitis and ichthyosis, while CLDN16 and CLDN19 mutations are considered to be related to hypomagnesemia and hypercalcinuria.

Differential expression of CLDN protein is thought to be associated with various cancers. CLDN1 and CLDN7 are down-regulated in invasive breast cancer, prostate cancer and esophageal cancer, while CLDN3/4 are found to be up-regulated to varying degrees in cervical cancer, colon cancer, esophageal cancer, gastric cancer and other cancers. Sahin et al. found that in normal tissues, the isoform 2 subtype of CLDN18 (CLDN18.2) was only expressed in the differentiated epidermal cells of the gastric mucosa, but not in the area of gastric stem cells, while abnormally high expression was found in primary gastric cancer and its metastases. High expression of CLDN18.2 has also been reported in pancreatic cancer, esophageal cancer and lung cancer. Because CLDN18.2 is located on the surface of cell membrane, its biological function and characteristics determine that it is an ideal therapeutic target. In recent years, monoclonal antibodies against this target have also appeared, and among them, IMAB362 (Claudiximab) of Ganymed Company is the fastest developing one. IMAB362 binds CLDN18.2 on the surface of tumor cells, inducing antibody-dependent cytotoxicity (ADCC) and complement-dependent cytotoxicity (CDC), thus killing tumor cells. When combined with chemotherapy, IMAB362 can also enhance T cell infiltration and up-regulate pro-inflammatory factors.

SUMMARY OF THE INVENTION

The purpose of the present invention is to provide an anti-CLDN antibody, a pharmaceutical composition thereof and a detection method therefor.

The present invention adopts the following technical solutions.

An anti-CLDN antibody which comprises a heavy chain and a light chain:

wherein, the heavy chain of the antibody contains one or more CDRs, and the CDR of the heavy chain is no more than three amino acids different from the CDR sequence of any one of SEQ ID No: 1 to SEQ ID No: 7 or any one of SEQ ID No: 15 to SEQ ID No: 30, the light chain of the antibody contains one or more CDRs, and the CDR of the light chain is no more than three amino acids different from the CDR sequence of any one of SEQ ID No: 8 to SEQ ID No: 14 or any one of SEQ ID No: 31 to SEQ ID No: 46.

Further, the anti-CLDN antibody of the present invention has a feature that the heavy chain of the antibody is selected from any one of SEQ ID No: 1 to No. 7.

Further, the anti-CLDN antibody of the present invention has a feature that the light chain of the antibody is selected from any one of SEQ ID No: 8 to SEQ ID No: 14 or any one of SEQ ID No: 31 to SEQ ID No: 46.

Further, the anti-CLDN antibody of the present invention has a feature that the heavy chain of the antibody is selected from any one of SEQ ID No: 15 to SEQ ID No: 30.

Further, the anti-CLDN antibody of the present invention has a feature that the light chain of the antibody is selected from any one of SEQ ID No: 31 to SEQ ID No: 46.

Further, the anti-CLDN antibody of the present invention has a feature that the heavy chain and the light chain of the antibody form a combination selected from the group consisting of:

SEQ ID No: 1 and SEQ ID No: 8, SEQ ID No: 2 and SEQ ID No: 9, SEQ ID No: 3 and SEQ ID No: 10, SEQ ID No: 4 and SEQ ID No: 11, SEQ ID No: 5 and SEQ ID No: 12, SEQ ID No: 6 and SEQ ID No: 13, SEQ ID No: 7 and SEQ ID No: 14, SEQ ID No: 15 and SEQ ID No: 31, SEQ ID No: 16 and SEQ ID No: 32, SEQ ID No: 17 and SEQ ID No: 33, SEQ ID No: 18 and SEQ ID No: 34, SEQ ID No: 19 and SEQ ID No: 35, SEQ ID No: 20 and SEQ ID No: 36, SEQ ID No: 21 and SEQ ID No: 37, SEQ ID No: 22 and SEQ ID No: 38, SEQ ID No: 23 and SEQ ID No: 39, SEQ ID No: 24 and SEQ ID No: 40, SEQ ID No: 25 and SEQ ID No: 41, SEQ ID No: 26 and SEQ ID No: 42, SEQ ID No: 27 and SEQ ID No: 43, SEQ ID No: 28 and SEQ ID No: 44, SEQ ID No: 29 and SEQ ID No: 45, SEQ ID No: 30 and SEQ ID No: 46.

The present invention also provides a polynucleotide encoding the antibody as defined hereinabove.

The present invention also provides a pharmaceutical composition comprising any one of the above antibodies.

The present invention also provides the application of any one of the above-mentioned antibodies in the preparation of anti-tumor drugs.

The present invention also provides a method for detecting the presence or absence of CLDN in a biological sample, which comprises the steps of administering an antibody as described in any one of the above to the biological sample, wherein the antibody has a detectable label, and the steps of detecting the presence or absence of the detectable label or detecting the content of the detectable label.

Beneficial Effects of the Invention

The anti-CLDN antibody of the present invention has stronger binding ability with cells than IMAB362. Moreover, the antibody of the present invention shows better effect of inhibiting tumor growth than IMAB362 in animal pharmacodynamics in vivo.

DESCRIPTION OF DRAWINGS

FIG. 1E shows the binding ability of antibody QP196198 screened out from hybridoma to CHOS cells FIG. 1F shows the binding ability of antibody QP199200 screened out from hybridoma to CHOS cells FIG. 1G shows the binding ability of antibody QP201202 screened out from hybridoma to CHOS cells FIG. 1H shows the binding ability of antibody QP207208 screened out from hybridoma to CHOS cells

FIG. 3C shows the binding ability of antibody QP11091110 screened out from phage to CHOS cells.

FIG. 3D shows the binding ability of antibody QP11111112 screened out from phage to CHOS cells.

FIG. 3E shows the binding ability of antibody QP11131114 screened out from phage to CHOS cells.

FIG. 3F shows the binding ability of antibody QP11151116 screened out from phage to CHOS cells.

FIG. 4A shows the binding ability of antibody QP11171118 screened out from phage to CHOS cells.

FIG. 4B shows the binding ability of antibody QP11031104 screened out from phage to CHOS cells.

FIG. 4C shows the binding ability of antibody QP10451046 screened out from phage to CHOS cells.

FIG. 4D shows the binding ability of antibody QP10471048 screened out from phage to CHOS cells.

FIG. 5A shows the binding ability of control antibody QP024025 to different 293T transient cell lines.

FIG. 5B shows the binding ability of antibody QP188189 screened out from hybridoma to different 293T transient cell lines.

FIG. 5C shows the binding ability of antibody QP190191 screened out from hybridoma to different 293T transient cell lines.

FIG. 5D shows the binding ability of antibody QP192193 screened out from hybridoma to different 293T transient cell lines.

Figures 1A, 1B, 1C, 1D:
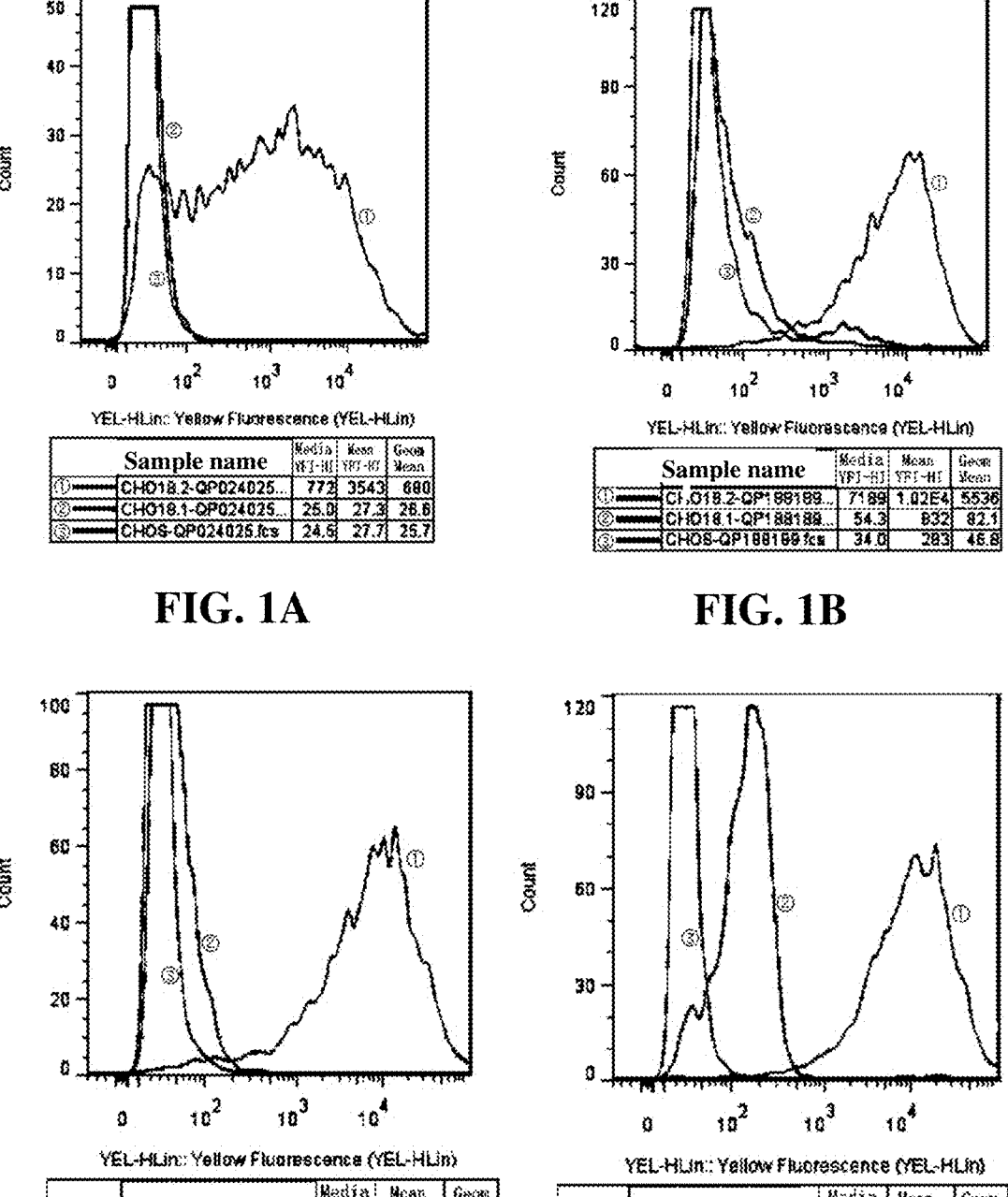
FIG. 1A shows the binding ability of control antibody QP024025 to CHOS cells
FIG. 1B shows the binding ability of antibody QP188189 screened out from hybridoma to CHOS cells
FIG. 1C shows the binding ability of antibody QP190191 screened out from hybridoma to CHOS cells
FIG. 1D shows the binding ability of antibody QP192193 screened out from hybridoma to CHOS cells
Figure 2A:
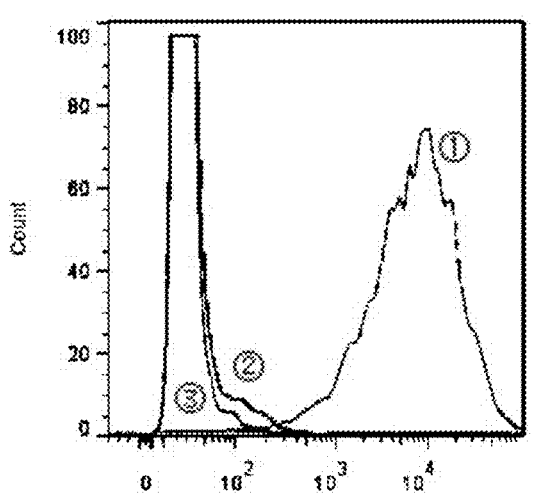
FIG. 2A shows the binding ability of antibody QP10731074 screened out from phage to CHOS cells.
Figure 2B:
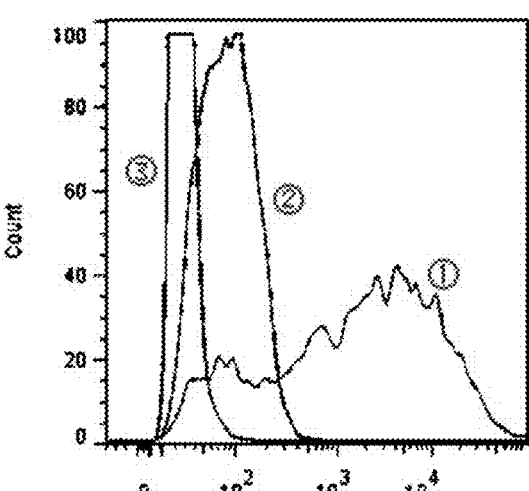
FIG. 2B shows the binding ability of antibody QP10791080 screened out from phage to CHOS cells.
Figure 2C:
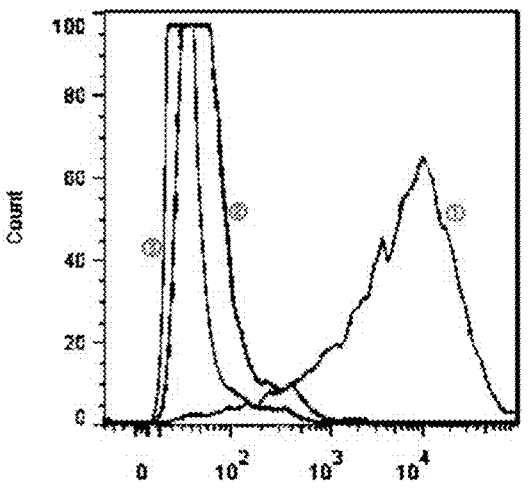
FIG. 2C shows the binding ability of antibody QP10851086 screened out from phage to CHOS cells.
Figure 2D:
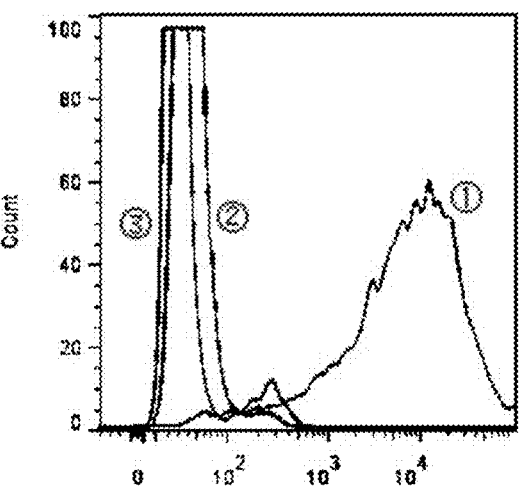
FIG. 2D shows the binding ability of antibody QP10911092 screened out from phage to CHOS cells.
Figure 2E:
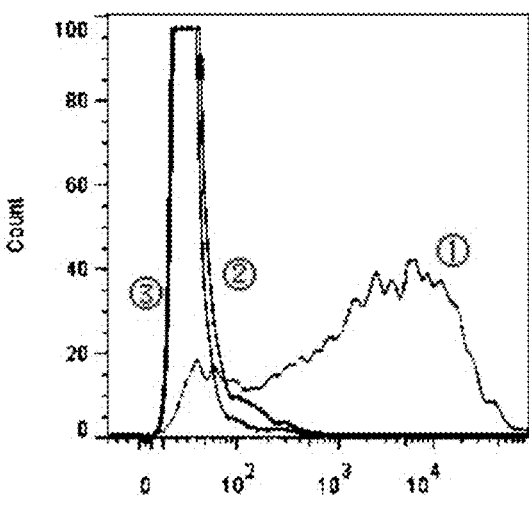
FIG. 2E shows the binding ability of antibody QP10971098 screened out from phage to CHOS cells.
Figure 2F:
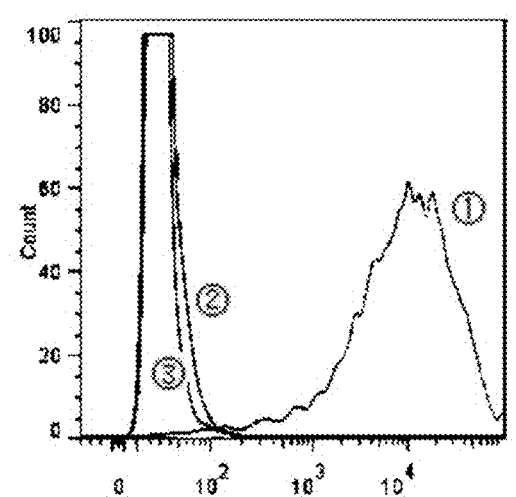
FIG. 2F shows the binding ability of antibody QP10991100 screened out from phage to CHOS cells.
Figure 3A:
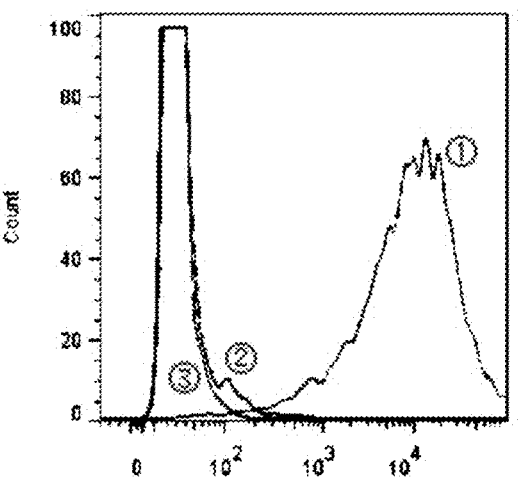
FIG. 3A shows the binding ability of antibody QP11051106 screened out from phage to CHOS cells.
Figure 3B:
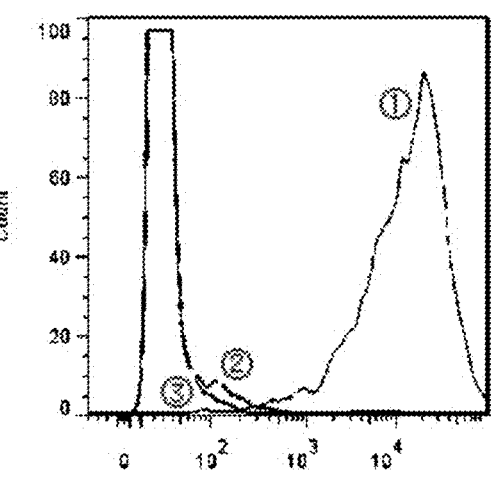
FIG. 3B shows the binding ability of antibody QP11071108 screened out from phage to CHOS cells.
Figure 5E:
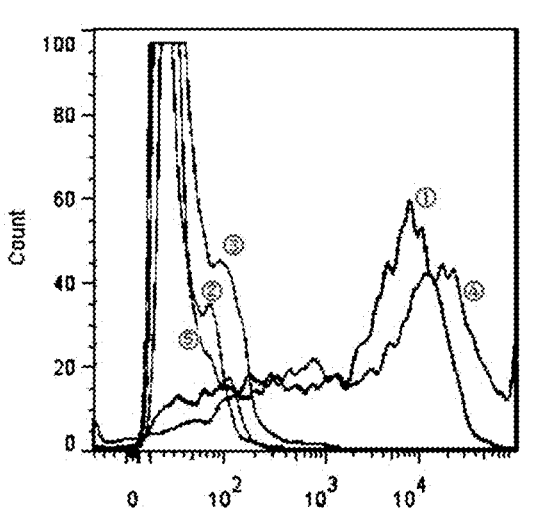

FIG. 5E shows the binding ability of antibody QP196198 screened out from hybridoma to different 293T transient cell lines.

Figure 5F:
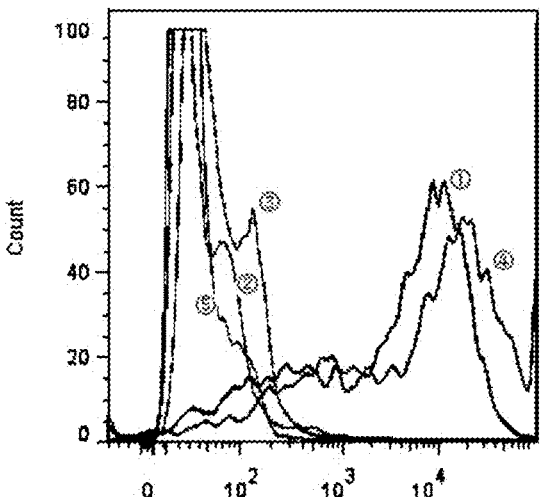

FIG. 5F shows the binding ability of antibody QP199200 screened out from hybridoma to different 293T transient cell lines.

Figure 5G:
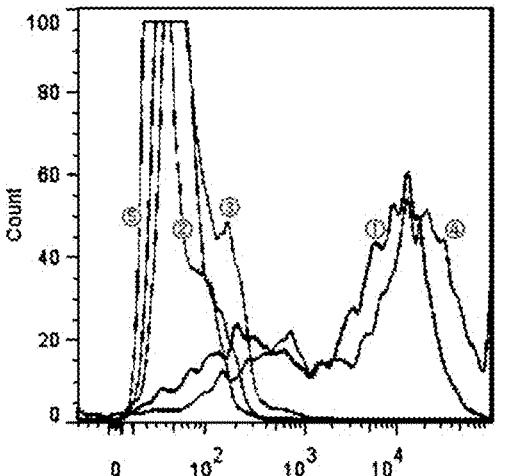

FIG. 5G shows the binding ability of antibody QP201202 screened out from hybridoma to different 293T transient cell lines.

Figure 5H:
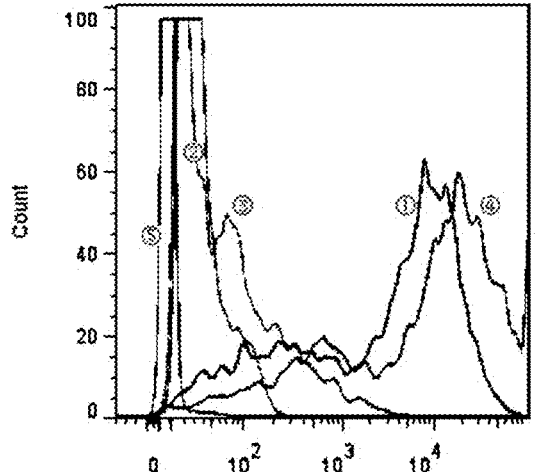

FIG. 5H shows the binding ability of antibody QP207208 screened out from hybridoma to different 293T transient cell lines.

FIG. 6A shows the binding ability of antibody QP10451046 screened out from phage to different 293T transient cell lines.

FIG. 6B shows the binding ability of antibody QP10711072 screened out from phage to different 293T transient cell lines.

FIG. 6C shows the binding ability of antibody QP10731074 screened out from phage to different 293T transient cell lines.

FIG. 6D shows the binding ability of antibody QP10851086 screened out from phage to different 293T transient cell lines.

Figure 6E:
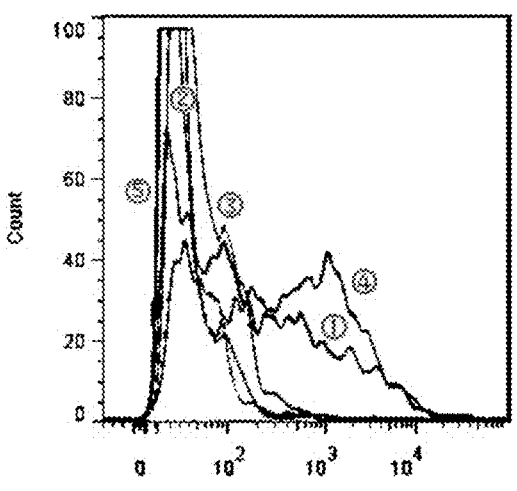

FIG. 6E shows the binding ability of antibody QP10911092 screened out from phage to different 293T transient cell lines.

Figure 6F:
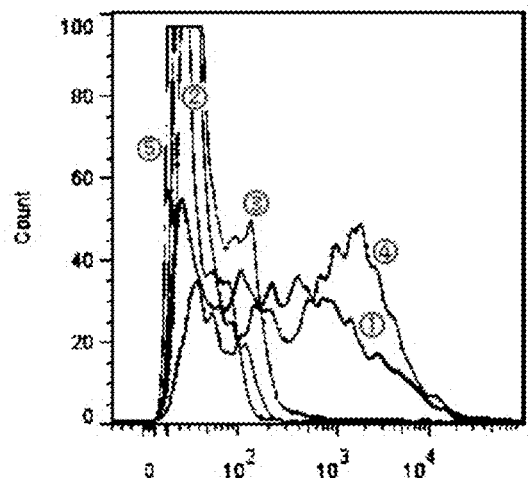

FIG. 6F shows the binding ability of antibody QP10991100 screened out from phage to different 293T transient cell lines.

Figure 6G:
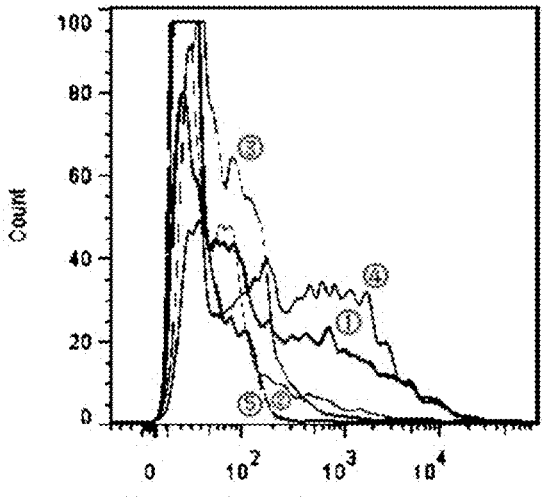

FIG. 6G shows the binding ability of antibody QP11031104 screened out from phage to different 293T transient cell lines.

Figure 6H:
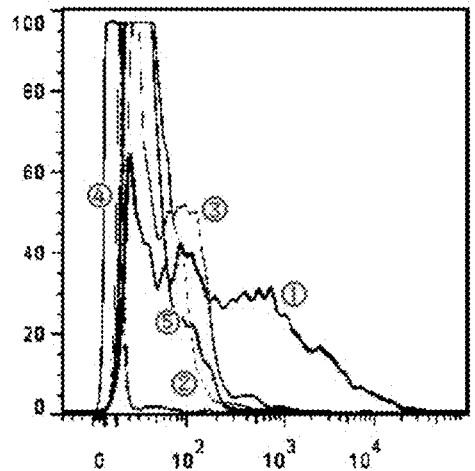

FIG. 6H shows the binding ability of antibody QP11051106 screened out from phage to different 293T transient cell lines.

Figure 7A:
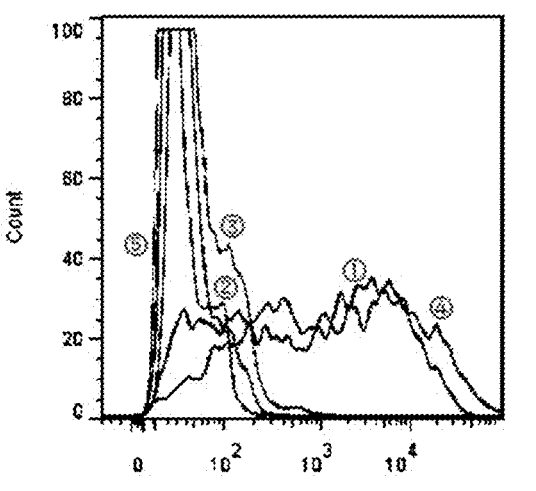

FIG. 7A shows the binding ability of antibody QP11071108 screened out from phage to different 293T transient cell lines.

Figure 7B:
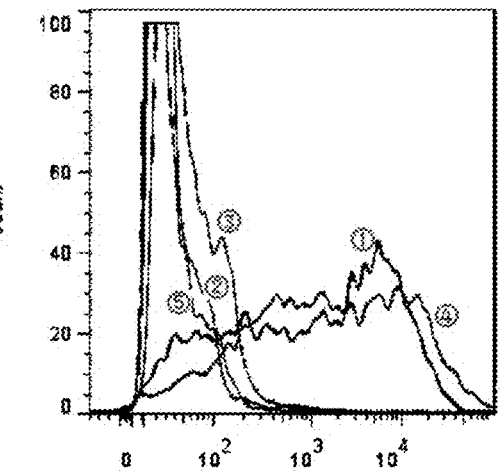

FIG. 7B shows the binding ability of antibody QP11091110 screened out from phage to different 293T transient cell lines.

Figure 7C:
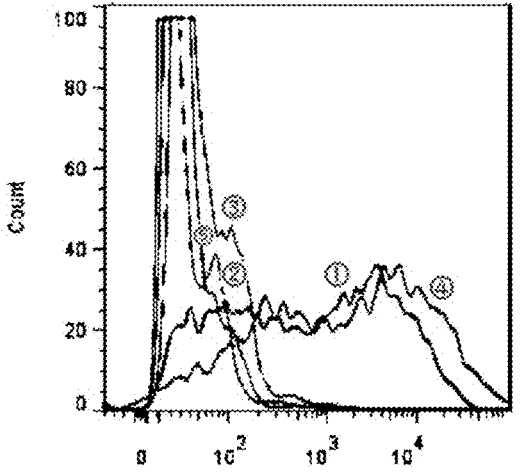

FIG. 7C shows the binding ability of antibody QP11111112 screened out from phage to different 293T transient cell lines.

Figure 7D:
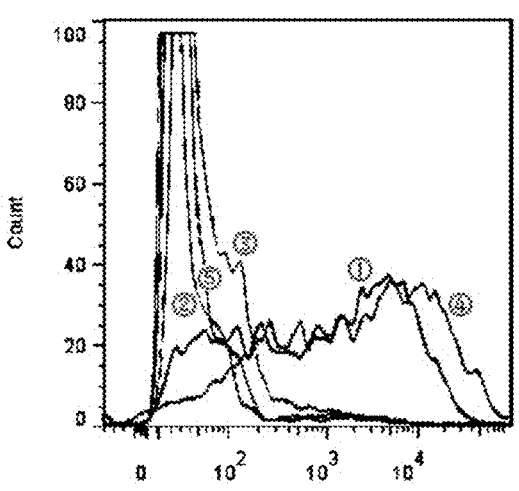

FIG. 7D shows the binding ability of antibody QP11131114 screened out from phage to different 293T transient cell lines.

FIG. 7E shows the binding ability of antibody QP11151116 screened out from phage to different 293T transient cell lines.

FIG. 7F shows the binding ability of antibody QP11171118 screened out from phage to different 293T transient cell lines.

FIG. 8A is the curve of control group IMAB362 in the experiment of binding ability of control antibody to gastric cancer PDX model GA0006 tumor cells.

FIG. 8B is the curve of QP190191 in the experiment of binding ability of antibody to gastric cancer PDX model GA0006 tumor cells.

Figures 8C, 8D, 8E, 8F:
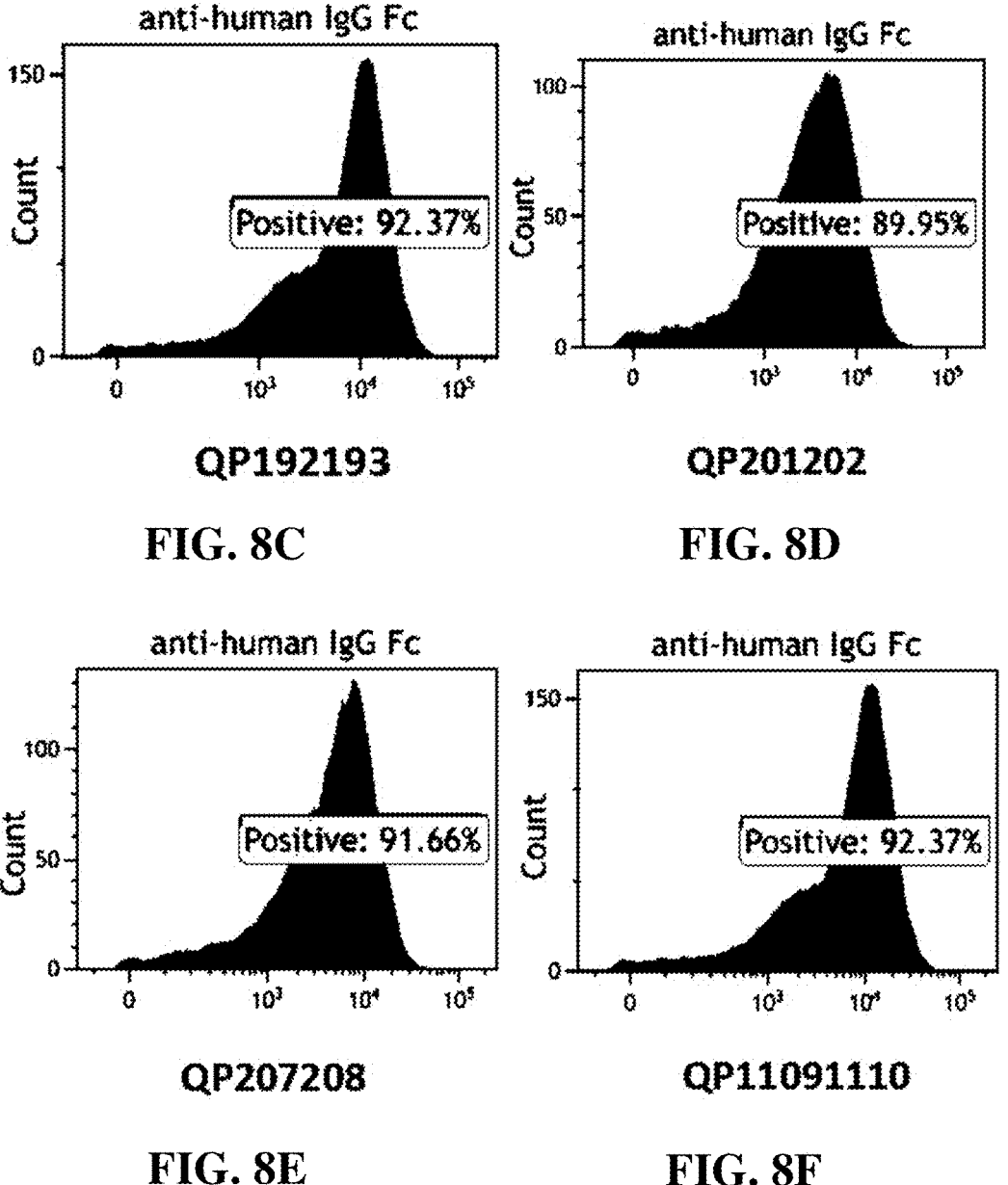

FIG. 8C is the curve of QP192193 in the experiment of binding ability of antibody to gastric cancer PDX model GA0006 tumor cells.

FIG. 8D is the curve of QP201202 in the experiment of binding ability of antibody to gastric cancer PDX model GA0006 tumor cells.

FIG. 8E is the curve of QP207208 in the experiment of binding ability of antibody to gastric cancer PDX model GA0006 tumor cells.

FIG. 8F is the curve of QP11091110 in the experiment of binding ability of antibody to gastric cancer PDX model GA0006 tumor cells.

FIG. 8G is the curve of QP11131114 in the experiment of binding ability of antibody to gastric cancer PDX model GA0006 tumor cells.

FIG. 8H is the curve of QP11151116 in the experiment of binding ability of antibody to gastric cancer PDX model GA0006 tumor cells.

FIG. 9 shows the pharmacodynamic test of the antibody against the gastric cancer PDX model GA0006.

Figure 10A:
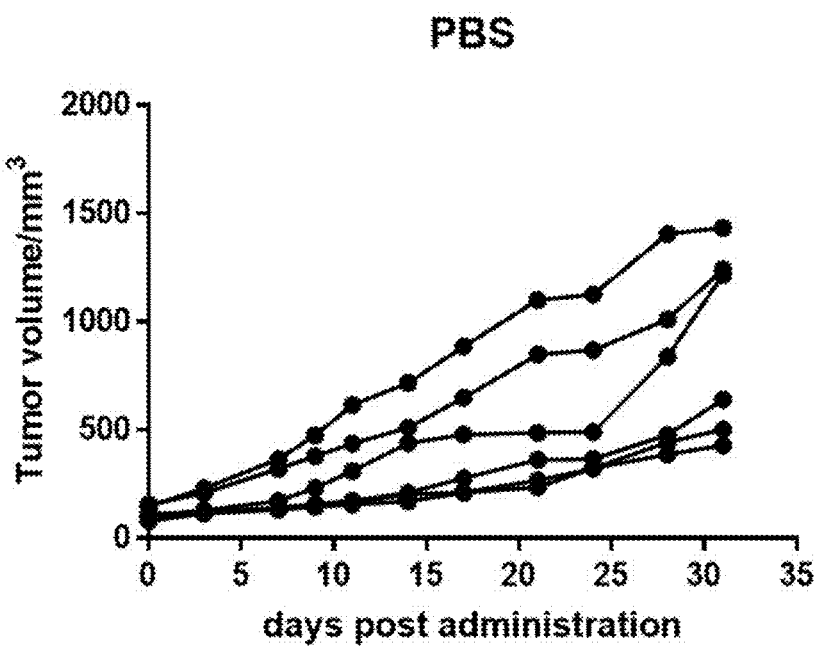

FIG. 10A is the tumor growth curve of PBS group (negative control) after grouping.

Figure 10B:
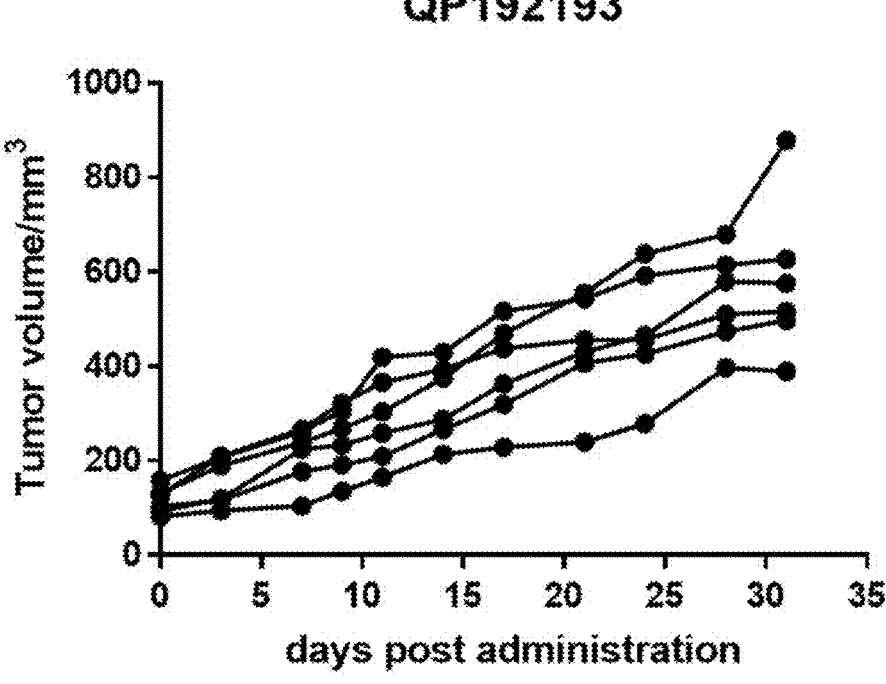

FIG. 10B is the tumor growth curve of QP192193 group after grouping.

Figure 10C:
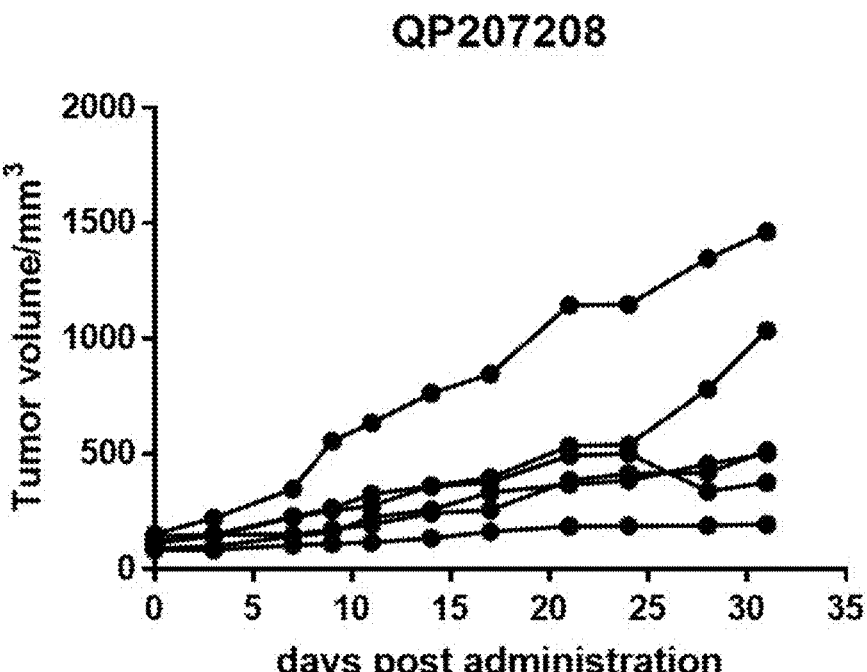

FIG. 10C is the tumor growth curve of QP207208 group after grouping.

Figure 10D:
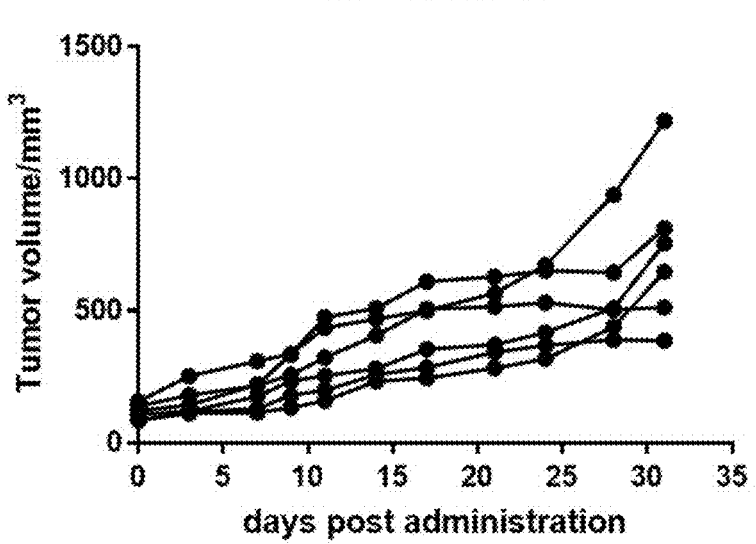

FIG. 10D is the tumor growth curve of QP11151116 group after grouping.

Figure 10E:
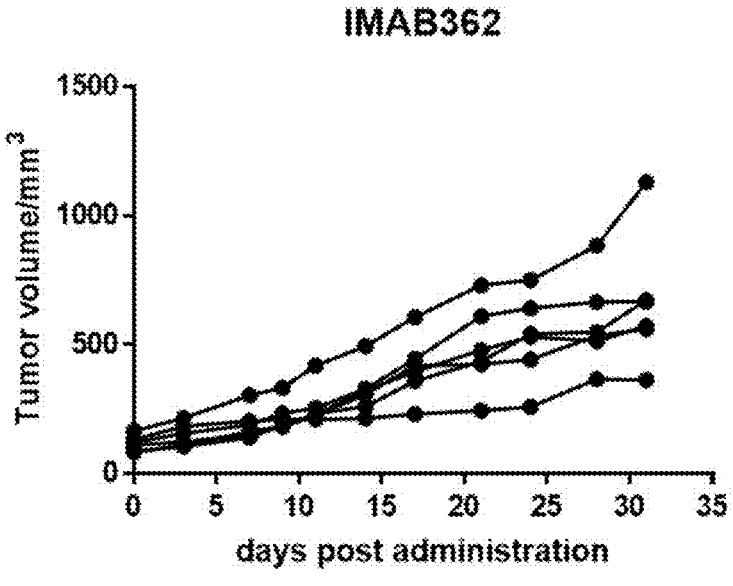

FIG. 10E is the tumor growth curve of the control antibody IMAB362 group after grouping.

Figure 11:
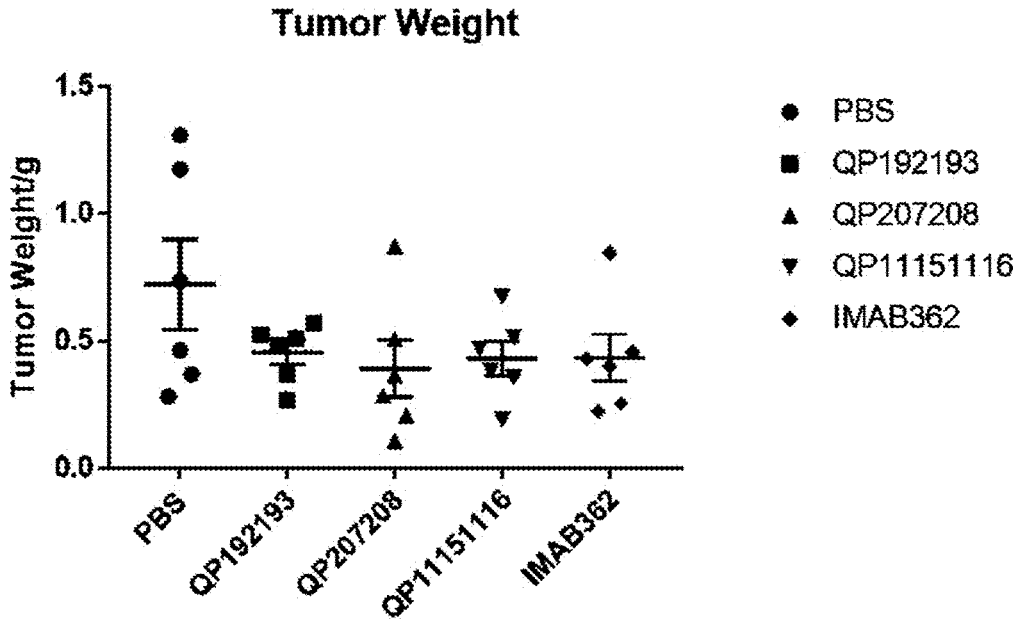

FIG. 11 shows the weight of tumor at D31 in each group of mice added with each antibody of the present invention and a control antibody.

Figure 12:
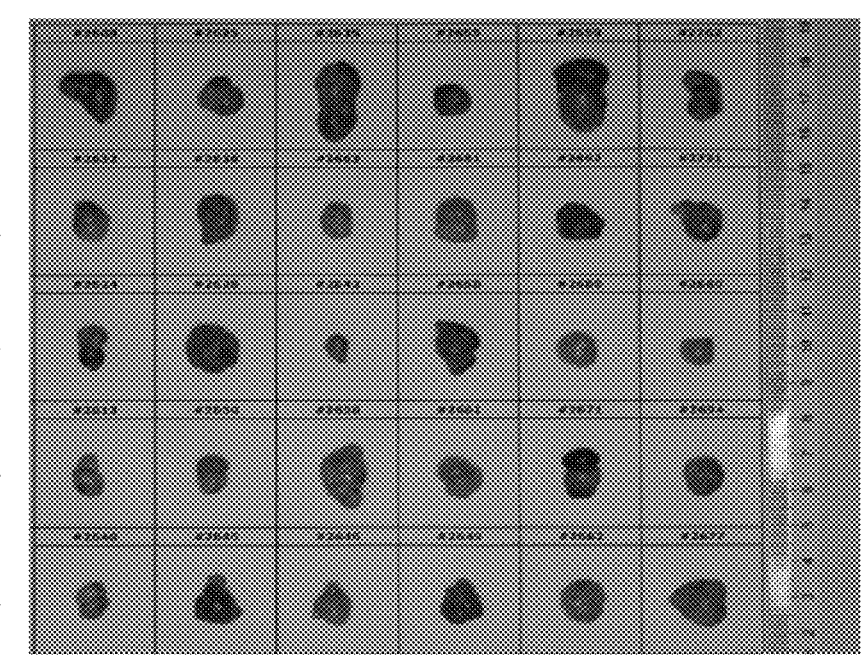

FIG. 12 is a real shot diagram of the tumor volume of each experimental group.

Figure 13:
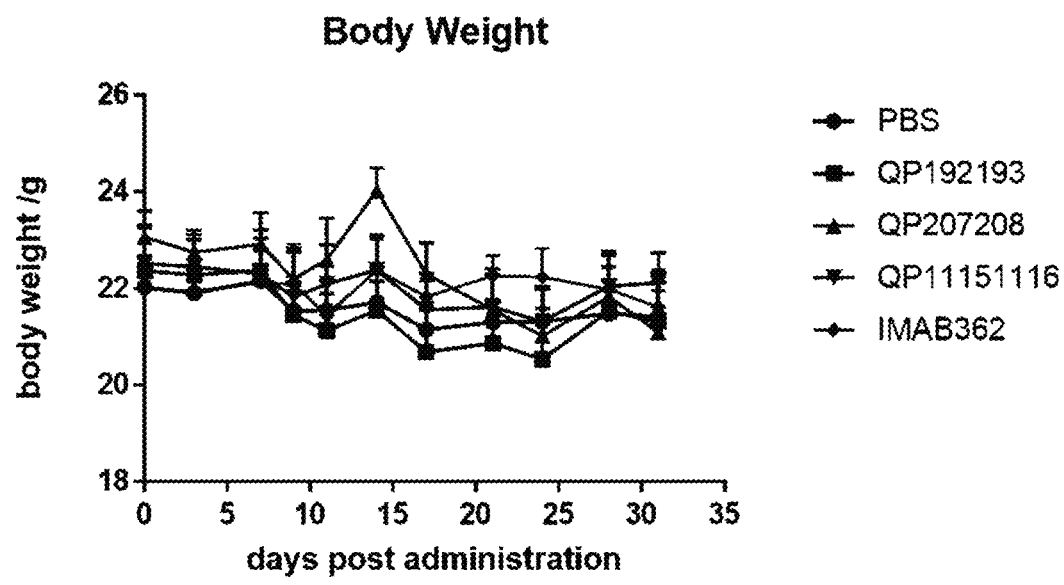

FIG. 13 is the body weight curve of mice in each group.

Figure 14:
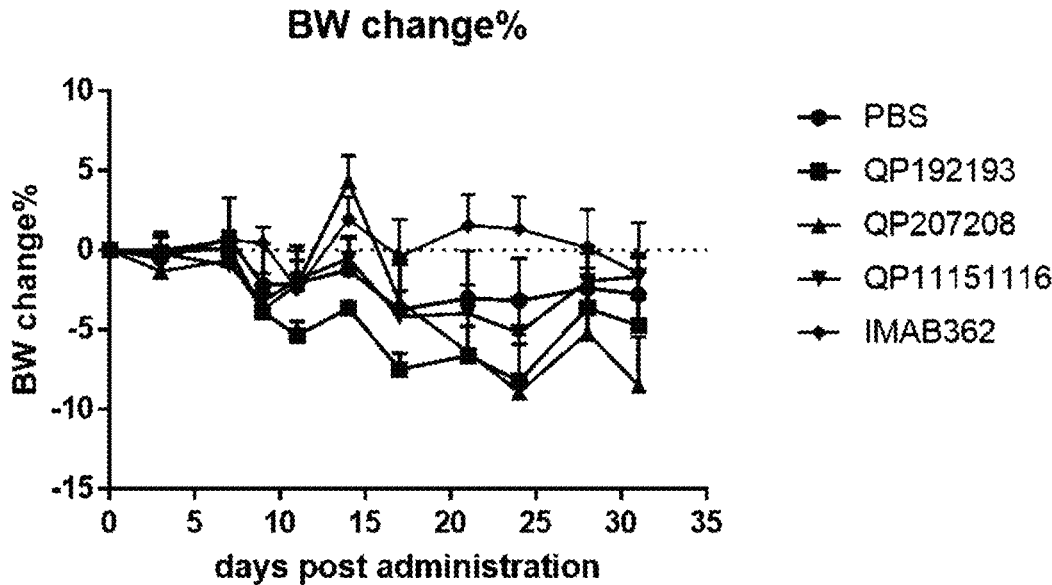

FIG. 14 is the curve of body weight change rate of mice in each group.

DETAILED DESCRIPTION

Specific embodiments of the present invention will be explained below with reference to the accompanying drawings.

Antibodies of the present invention include, but are not limited to, human antibodies. In various antibody screening methods provided by the present invention, the more convenient hybridoma screening antibody is usually preferred. However, the antigen of this target (claudin 18.2) is difficult to obtain, so the phage library is also used to screen the antibody. The sequences of the anti-claudin18.2 antibodies screened out in this embodiment are as follows:

For Antibodies Screened by Hybridoma, the CDRs in the Heavy Chain Variable Region (VH) are Shown in the Underlined Parts of the Sequences

```
> QP189
                                  (SEQ ID No: 1)
QVQLQQSGAELVKPGASVKLSCKASGYTFTSYGINWVRQRPEQGLEWIGWL

FPGDGTIKYNENFKGKATLTTDRSSSAAYMQLSRLTSEDSAVYFCARGGYY

GNAMDYWGQGTSVTVSS

> QP191
                                  (SEQ ID No: 2)
EVKLVESGGGLVKPGGSLKLSCAASGFTFSNYAMSWVRQTPEKRLEWVASI

ISGGRTYYLDSEKGRFTISRDNARNNLYLQMSSLRSEDTAMYYCTRIYYGN

SFDYWGQGTTLTVSS

> QD193
                                  (SEQ ID No: 3)
QVQLQQSGAELVRPGSSVKISCKASGYAFSSYWMNWVKQRPGQGLEWIGQI

YPGNGDTTYNGKFKGQATLTADKSSSTVYMQLSSLTSEDSAVYFCARFVKG

NAMDYWGQGTSVTVSS

> QD198
                                  (SEQ ID No: 4)
QVQLKESGPGLVAPSQSLSITCTVSGFSLTIYGVHWVRQPPGRGLEWLGVI

WAGGSTNYNSALMSRLSISKDNSKSQVFLKVNSLQTDDTAMYYCARDYYYG

SGFDYWGQGTTLTVSS

> QD200
                                  (SEQ ID No: 5)
DVQLVESGGGLVQPGGSRKLSCAASGFTFSSFGMHWVRQAPEKGLEWVAYI

SSGSNSIYYVDTVKGRFTISRDNPKNTLFLQMTSLKSEDTAMYYCARNAYY

GNSFDYWGQGTTLTVSS

> QD202
                                  (SEQ ID No: 6)
EVQLQQSGPELVKPGASVKMSCKASGYTFTNYFVHWVKQKPGQGLEWIGYI

NPYNDDTKYNEKFKGKATLTSDKSSSTAYMDLSSLTSEDSAVYYCLSLRFF

AYWGQGTLVTVSA

> QD208
                                  (SEQ ID No: 7)
EVQLQQSGPELVKPGASVKMSCKASGYTFTSYIMHWVKQKPGQGLEWIGYI

NPYNDGTKYNEKFKGKATLTSDKSSSTVYMELSSLTSEDSAVYCCARLGFT

TRNAMDYWGQGTSVTVSS
```

Light Chain Sequence:

The CDRs in the light chain variable region (VL) are shown in the underlined parts of the sequences.

```
> QD188
                                  (SEQ ID No: 8)
DIVMTQSPSSLTVTAGEKVTMSCKSSQSLLNSGNQKSYLTWYQQKPGQPPK

LLIYWASTRESGVPDRFTGSGSGTDFTLTISSVQAEDLAVYFCQNDYFYPY

TFGGGTKLEIK

> QD190
                                  (SEQ ID No: 9)
DIVMTQSPSSQTVTAGEKVTMSCKSSQSLLNSGNQKNYLTWYQQKPGQPPK

LLIYWASTRESGVPDRFTGSGSGTDFTLTISNMQAEDLAVYYCQNDYSYPF

TFGSGTKLEIK
```

-continued

> QD192

(SEQ ID No: 10)

DIVMTQSPSSLTVTAGEKVTMSCKSSQSLLNSGNQKNYLTWYQQNPGQPPK

MLIYWASTRESGVPDRFTGSGSGIDFSLTISSVQAEDLALYYCQNAYSYPF

TFGSGTKLEIK

> QD196

(SEQ ID No: 11)

DIVMTQSPSSLSVSAGEKVTMSCKSSQSLLNSGNQKNYLAWYQQKPGQPPK

LLIYGASTRESGVPDRFTGSGSGTDFTLTISSVRAEDLAVYYCQNDHYYPF

TFGSGTKLEIK

> QD199

(SEQ ID No: 12)

DIVMTQSPSSLTVTAGEKVTMSCKSSQSLLNSGNQKNYLTWYQQKPGQPPK

LLIYWASTRESGVPDRFTGSGSGTVFTLTISSVQAEDLAVYFCQNNYYYPL

TFGAGTKLELK

> QD201

(SEQ ID No: 13)

DIVMTQSPSSLTVTAGEKVTMSCKSSQSLLNSGNQKNYLTWYQQKPGQAPK

LLIYWASTRESGVPDRFIGSGSGTDFTLTISHVQAEDLAVYFCQNDYSYPL

TFGAGTNLELK

> QD207

(SEQ ID No: 14)

DIVMTQSPSSLSVSAGEKVTMNCKSSQSLLNSGNQKNYLAWYQQKPGQPPK

LLIYGASTRESGVPDRFTGSGSGTDFTLTISSVQAEDLAVYYCQNDHSYPF

TFGSGTKLEIK

For Antibodies Screened by Phage Library, the CDRs in the Heavy Chain Variable Region (VH) are Shown in the Underlined Parts of the Sequences

> QD1045

(SEQ ID No: 15)

QVQLVQSGAEVKKPGASVKVSCKASGYTFTSYYMHWVRQAPGQGLEWMGII

NPSGGSTSYAQKFQGRVTMRDTSTSTVYMELSSLRSEDTAVYYCARDYAF

TGFDYWGQGTLVTVSS

> QD1047

(SEQ ID No: 16)

QVQLVQSGAEVKKPGASVKVSCKASGYTFTSYYMHWVRQAPGQGLEWMGII

NPSGGSTSYAQKFQGRVTMRDTSTSTVYMELSSLRSEDTAVYYCARSSAY

GTYSMDYWGQGTLVTVSS

> QD1073

(SEQ ID No: 17)

QVQLVQSGAEVKKPGSSVKVSCKASGGTFSSYAISWVRQAPGQGLEWMGGI

IPIFGTANYAQKFQGRVTITADKSTSTAYMELSSLRSEDTGVYYCARGSGS

WFGPYFDYWGQGTTVTVSS

> QD1079

(SEQ ID No: 18)

QVQLVQSGAEVKKPGSSVKVSCKASGGTFSSYAISWVRQAPGQGLEWMGGI

IPIFGTANYAQKFQGRVTITADKSTSTAYMELSSLRSEDTAVYYCARTDGA

TPFDYWGQGTTVTVSS

-continued

> QD1085

(SEQ ID No: 19)

QVQLVQSGAEVKKPGSSVKVSCKASGGTFSSYAISWVRQAPGQGLEWMGGI

IPIFGTANYAQKFQGRVTITADKSTSTAYMELSSLRSEDTAVYYCARRSYY

GTGAFDYWGQGTTVTVSS

> QD1091

(SEQ ID No: 20)

QVQLVQSGAEVKKPGSSVKVSCKASGGTFSSYAISWVRQAPGQGLEWMGGI

IPIFGTANYAQKFQGRVTITADKSTSTAYMELSSLRSEDTAVYYCARSLGY

FSGLAFDYWGQGTTVTVSS

> QD1097

(SEQ ID No: 21)

QVQLVQSGAEVKKPGSSVKVSCKASGGTFSSYAISWVRQAPGQGLEWMGGI

IPIFGTANYAQKFQGRVTITADKSTSTAYMELSSLRSEDTAVYYCARGYNW

SFGMDYWGQGTTVTVSS

> QD1099

(SEQ ID No: 22)

QVQLVQSGAEVKKPGSSVKVSCKASGGTFSSYAISWVRQAPGQGLEWMGGI

IPIFGTANYAQKFQGRVTITADKSTSTAYMELSSLRSEDTAVYYCARAGYF

PRSLDYWGQGTTVTVSS

> QD1103

(SEQ ID No: 23)

QVQLVQSGAEVKKPGSSVKVSCKASGGTFSSYAISWVRQAPGQGLEWMGGI

IPIFGTANYAQKFQGRVTITADKSTSTAYMELSSLRSEDTAVYYCARGYSW

YWLFGFDYWGQGTTVTVSS

> QD1105

(SEQ ID No: 24)

QVQLVQSGAEVKKPGSSVKVSCKASGGTFSSYAISWVRQAPGQGLEWMGGI

IPIFGTANYAQKFQGRVTITADKSTSTAYMELSSLRSEDTAVYYCARGGDW

GGYMDYWGQGTTVTVSS

> QD1107

(SEQ ID No: 25)

EVQLLESGGGLVQPGGSLRLSCAASGFTFSSYAMSWVRQAPGKGLEWVSAI

SGSGGSTYYADSVKGRFTISRDNSKNTLYLQMNSLRAEDTAVYYCARDYYY

YFWFDYWGQGTLVTVSS

> QD1109

(SEQ ID No: 26)

EVQLLESGGGLVQPGGSLRLSCAASGFTFSSYAMSWVRQAPGKGLEWVSAI

SGSGGSTYYADSVKGRFTISRDNSKNTLYLQMNSLRAEDTAVYYCARDYYY

YYWFDYWGQGTLVTVSS

> QD1111

(SEQ ID No: 27)

EVQLLESGGGLVQPGGSLRLSCAASGFTFSSYAMSWVRQAPGKGLEWVSAI

SGSGGSTYYADSVKGRFTISRDNSKNTLYLQMNSLRAEDTAVYYCAKGYYY

YFWFDYWGQGTLVTVSS

> QD1113

(SEQ ID No: 28)

EVQLLESGGGLVQPGGSLRLSCAASGFTFSSYAMSWVRQAPGKGLEWVSAI

SGSGGSTYYADSVKGRFTISRDNSKNTLYLQMNSLRAEDTAVYYCAKSAAY

YYFWFDYWGQGTLVTVSS

-continued

> QD1115

(SEQ ID No: 29)

EVQLLESGGGLVQPGGSLRLSCAASGFTFSSYAMSWVRQAPGKGLEWVSAI

SGSGGSTYYADSVKGRFTISRDNSKNTLYLQMNSLRAEDTAVYYCARDSYY

YYFWYDYWGQGTLVTVSS

> QD1117

(SEQ ID No: 30)

EVQLLESGGGLVQPGGSLRLSCAASGFTFSSYAMSWVRQAPGKGLEWVSAI

SGSGGSTYYADSVKGRFTISRDNSKNTLYLQMNSLRAEDTAVYYCAKAIDY

YTFDYWGQGTLVTVSS

Light Chain Sequence:

The CDRs in the Light Chain Variable Region (VL) are Shown in the Underlined Parts of the Sequences.

> QD1046

(SEQ ID No: 31)

DIVMTQSPLSLPVTPGEPASISCRSSQSLLHSNGYNYLDWYLQKPGQSPQL

LIYLGSNRASGVPDRFSGSGSGTDFTLKISRVEAEDVGVYYCMQALMTPTF

GQGTKVEIK

> QD1048

(SEQ ID No: 32)

DIVMTQSPLSLPVTPGEPASISCRSSQSLLHSNGYNYLDWYLQKPGQSPQL

LIYLGSNRASGVPDRFSGSGSGTDFTLKISRVEAEDVGVYYCMQDLWPRTF

GQGTKVEIK

> QD1074

(SEQ ID No: 33)

DIVMTQSPLSLPVTPGEPASISCRSSQSLLHSNGYNYLDWYLQKPGQSPQL

LIYLGSNRASGVPDRFSGSGSGTDFTLKISRVEAEDVGVYYCMQAAQSPTF

GQGTKVEIK

> QD1080

(SEQ ID No: 34)

DIVMTQSPLSLPVTPGEPASISCRSSQSLLHSNGYNYLDWYLQKPGQSPQL

LIYLGSNRASGVPDRFSGSGSGTDFTLKISRVEAEDVGVYYCMQALNTPPT

FGQGTKVEIK

> QD1086

(SEQ ID No: 35)

DIVMTQSPLSLPVTPGEPASISCRSSQSLLHSNGYNYLDWYLQKPGQSPQL

LIYLGSNRASGVTDRFSGSGSGTDFTLKISRVEAEDVGVYYCMQALMTPTF

GQGTKVEIK

> QD1092

(SEQ ID No: 36)

DIVMTQSPLSLPVTPGEPASISCRSSQSLLHSNGYNYLDWYLQKPGQSPQL

LIYLGSNRASGVPDRFSGSGSGTDFTLKISRVEAEDVGVYYCMQGRQFPTF

GQGTKVEIK

> QD1098

(SEQ ID No: 37)

DIVMTQSPLSLPVTPGEPASISCRSSQSLLHSNGYNYLDWYLQKPGQSPQL

LIYLGSNRASGVPDRFSGSGSGTDFTLKISRVEAEDVGVYYCMQGLNTFTF

GQGTKVEIK

-continued

> QD1100

(SEQ ID No: 38)

DIVMTQSPLSLPVTPGEPASISCRSSQSLLHSNGYNYLDWYLQKPGQSPQL

LIYLGSNRASGVPDRFSGSGSGTDFTLKISRVEAEDVGVYYCMQALQWDTF

GQGTKVEIK

> QD1104

(SEQ ID No: 39)

DIVMTQSPLSLPVTPGEPASISCRSSQSLLHSNGYNYLDWYLQKPGQSPQL

LIYLGSNRASGVPDRFSGSGSGTDFTLKISRVEAEDVGVYYCMQALQTGTF

GQGTKVEIK

> QD1106

(SEQ ID No: 40)

DIVMTQSPDSLAVSLGERATINCKSSQSVLYSSNNKNYLAWYQQKPGQPPK

LLIYWASTRESGVPDRFSGSGSGTDFTLTISSLQAEDVAVYYCQQYYTTPF

TFGQGTKVEIK

> QD1108

(SEQ ID No: 41)

DIQMTQSPSTLSASVGDRVTITCRASQSISSWLAWYQQKPGKAPKLLIYDA

SSLESGVPSRFSGSGSGTEFTLTISSLQPDDFATYYCQQYNSYSTFGQGTK

VEIK

> QD1110

(SEQ ID No: 42)

DIQMTQSPSTLSASVGDRVTITCRASQSISSWLAWYQQKPGKAPKLLIYDA

SSLESGVPSRFSGSGSGTEFTLTISSLQPDDFATYYCQQYSSYSPTFGQGT

KVEIK

> QD1112

(SEQ ID No: 43)

DIQMTQSPSTLSASVGDRVTITCRASQSISSWLAWYQQKPGKAPKLLIYDA

SSLESGVPSRFSGSGSGTKFTLTISSLQPDDFATYYCQQYSTYPLTFGQGT

KVEIK

> QD1114

(SEQ ID No: 44)

DIQMTQSPSTLSASVGDRVTITCRASQSISSWLAWYQQKPGKAPKLLIYDA

SSLESGVPSRFSGSGSGTEFTLTISSLQPDDFATYYCQQYLSYPPTFGQGT

KVEIK

> QD1116

(SEQ ID No: 45)

DIQMTQSPSTLSASVGDRVTITCRASQSISSWLAWYQQKPGKAPKLLIYDA

SSLESGVPSRFSGSGSGTEFTLTISSLQPDDFATYYCQQYNSYPLTFGQGT

KVEIK

> QD1118

(SEQ ID No: 46)

DIQMTQSPSTLSASVGDRVTITCRASQSISSWLAWYQQKPGKAPKLLIYDA

SSLESGVPSRFSGSGSGTEFTLTISSLQPDDFATYYCQQYSTYPLTFGQGT

KVEVK

Antibody Binding Ability Experiment:

Experiment 1: Detection of the binding ability of antibody to tumor cell line by FACS a) 96-well plate was planted with $2 \times 10^5$ cells per well, centrifuged at 1000×rpm for 5 minutes. Cells were washed once with 1×PBS, and excess liquid of supernatant was sucked out;

b) 3% BSA-PBS solution was added to block the cells and the cells were blocked at 4° C. for 60 minutes.

c) The antibody to be tested was diluted to 5 ug/ml with blocking solution, added into the wells, and incubated at 4° C. for 60 minutes.

d) The antibody was sucked out, and cells in each well were washed with 220 ul of 1×PBS for three times.

e) 50 ul of PE-anti-human FC (1:200 dilution) secondary antibody was added to each well, and incubated in the dark at 4° C. for 40 minutes.

f) The antibody was sucked out, and cells in each well were washed with 1×PBS for four times.

g) On-board detection was performed.

Experiment 2: Detection of the Binding Ability of Antibody to PDX Tissue Tumor Cell by FACS a) A gentleMACS™ C Tube and 3 ml of digestion buffer were prepared for each tumor. The digestion buffer was prepared according to the instructions of Tumor Dissemination Kit (miltenyibiotech, 130-096-730) and it was freshly prepared just before use.

b) The mice were sacrificed, the tumor was removed with cleaning tools, and the blood vessels, fat, fascia and other tissues attached to the tumor surface were removed after washing with 1×PBS. Each digestion tube could digest no more than 0.8 g of tumor tissue to ensure that the tumor tissue was completely digested by digestion buffer.

c) The tumor tissue was placed in the hole of 6-well plate, digestion buffer was added, and the tumor tissue was cut to small pieces of about 1 mm$^3$ with clean tweezers and scalpel.

d) The tissue pieces were put into a gentleMACS™ C Tube, the well plate was washed with residual digestion buffer, and it was transferred into the digestion tube together, and placed on the ice.

e) The digestion tube was put upside down into gentleMACS automatic tissue processor, and the program 37_c_m_TDK_1 was selected for digestion. After the program was over, the digestion tube was removed and centrifuged instantaneously at 300×g to collect the cells and remaining tissues.

f) The supernatant was discarded, and the cells and tissues were re-suspended with 1×PBS. The cell suspension was added to the cell strainer, which was placed in a 50 ml centrifuge tube, and the suspension was sifted with 10 ml PBS to become single cell suspension.

g) After centrifuged at 300×g for 5 minutes, the supernatant was removed, and 5 ml PBS was used to resuspend. Cell counting was performed and the cell concentration was adjusted to 1×10$^6$ cells per sample.

h) 100 ul of PBS solution with a concentration of 1 μg/ml Mouse BD Fc Block (CAT #553141) was added to each sample to re-suspend cells, 20 ul of human FcR Blocking Reagent was added, mixed well, and incubated in the dark at room temperature for 10 minutes.

i) 5 ug/ml of primary antibody was added and incubated in the dark at 4° C. for 60 minutes.

j) 2 ml of FACS wash buffer was added, and the cells were gently resuspended, centrifuged at 300×g for 5 minutes, and the supernatant was removed, that was repeated twice.

k) 100 ul of FACS wash buffer containing PE labeled human IgG Fc secondary antibody and dye was added to incubate cells in the dark for 60 minutes.

l) 2 ml of FACS wash buffer was added, and the cells were gently resuspended, centrifuged at 300×g for 5 minutes, and the supernatant was removed, that was repeated twice.

m) 200 ul of FACS wash buffer was used to resuspend the cells, and on-board detection was performed.

The hybridoma clone in CHOS system and phage clone in CHOS system in the experimental drawings refer to the binding ability of antibodies screened from hybridoma and phage to CHOS cells, respectively. In the figures, CHO18.2: CHOS cells transfected with the CLDN18.2 gene for establishment of stable CHOS-CLDN18.2 cells, CHO18.1: CHOS cells transfected with the CLDN18.1 gene for establishment of stable CHOS-CLDN18.1 cells, CHOS:CHOS cells transfected with empty vector.

CHOS is a cell line obtained by immortalization of hamster ovary cells. FACS (Flow Cytometry Fluorescence Sorting Technique) was used to detect the binding ability of antibody to the cell line.

FIGS. 1A to 1H show the binding ability of antibodies screened by hybridoma to CHOS cells.

FIGS. 2A to 2H, 3A to 3H, and 4A to 4D show the binding ability of phage-screened antibodies to CHOS cells.

Purpose: To verify the binding ability of antibody to claudin18.1 (nonspecific binding) and claudin18.2 in CHOS cell lines.

In the figures of CHOS cell lines, each panel is composed of FACS detection results of three CHOS cell lines with one antibody to be tested, wherein:

1. The red curve (3) indicates the binding ability of the antibody to be tested to the CHOS cell line (CHOS) transfected with the empty vector, that is, the negative control;

2. The blue curve (2) indicates the binding ability of the antibody to be tested to the CHOS cell line transfected with claudin 18.1 (CHO18.1), that is, the detection of non-specific binding.

3. The yellow curve (1) indicates the binding ability of the antibody to be tested to the CHOS cell line transfected with claudin 18.2 (CHO 18.2), that is, the detection of binding ability of the target protein.

FIGS. 5A to 5H show the binding ability of antibodies screened by hybridoma to 293T cells.

FIGS. 6A to 6H and FIGS. 7A to 7F show the binding ability of phage-screened antibodies to CHOS cells.

In the figures, 293T-QD012:293T transiently transfected with CLDN18.1.

293T-QD010:293T transiently transfected with CLDN18.2

Purpose: To verify the binding ability of antibody to claudin18.1 (non-specific binding) and claudin18.2 in 293-T cell line.

293T-QD210:293T-CLDN18.2-18.1 ECD1 transient cells (293T transiently transfected with CLDN18.2-18.1 ECD1, the first extracellular domain of CLDN 18.2 was replaced by the first extracellular domain of CLDN 18.1).

293T-QD211:293T-CLDN18.1-18.2 ECD1 transient cells ((293T transiently transfected with CLDN18.1-18.2 ECD1, the first extracellular domain of CLDN 18.1 was replaced by the first extracellular domain of CLDN 18.2).

Purpose: To verify that the antibody binding region is the domain encoded by claudin 18.2 exon-1 in 293-T cell line.

Hybridoma clone in 293T and phage clone in 293T similarly refer to the antibodies screened from hybridoma and phage based binding ability to different 293T transient cell lines, respectively.

The purpose of the experiment in 293T is the same as in CHO cell line, and the meanings of each curve and its representation are explained as follows.

1. The red curve (5) indicates the binding ability of the antibody to be tested to the 293T cell line transiently transfected with empty vector, that is, the negative control.
2. The blue curve (4) indicates the binding of the antibody to be tested to the 293T cell line transiently transfected with claudin 18.2 (293T-QD010) to detect the binding ability of the target protein.
3. The orange curve (3) indicates the binding of the antibody to be tested to the 293T cell line transiently transfected with claudin18.1 (293T-QD012) to detect the non-specific binding.
4. The dark green curve (2) indicates the binding of the antibody to be tested to the 293T cell line transiently transfected with claudin18.1-18.2 ECD1 (the first extracellular domain of CLDN18.1 was replaced by the first extracellular domain of 18.2, which was the region where the antibody binding site was designed) (293T-QD211), to verify the domain of the antibody binding site.
5. The light green curve (1) indicates the binding of the antibody to be tested to the 293T cell line transiently transfected with claudin 18.2-18.1 ECD1 (the first extracellular domain of CLDN18.2 was replaced by the first extracellular domain of 18.1, the former was the region where the antibody binding site was designed) (293T-QD210), to verify the necessity of this domain for antibody binding.

FIGS. 8A to 8H show the binding ability of antibody to GA0006 tumor cells of gastric cancer PDX model.

TABLE 1

| Binding ratio of antibody to gastric cancer PDX model GA0006 tumor cells | |
| --- | --- |
| Antibody number | Ratio of antibody-bound cells |
| IMAB362 | 85.56% |
| QP190191 | 91.55% |
| QP192193 | 92.37% |
| QP201202 | 89.95% |
| QP207208 | 91.66% |
| QP11091110 | 92.37% |
| QP11131114 | 90.31% |
| QP11151116 | 91.66% |

The above experimental results show that the antibodies provided by the present invention have better binding ability to proteins and lower non-specific binding.

In other embodiments, the present invention also provides a polynucleotide encoding the antibody as described above. The polynucleotides encoding the antibodies provided by the present invention, when provided in the form of DNA, may contain non-coding sequences that will be removed during subsequent transcription and editing, or may only contain sequences encoding sequences corresponding to the antibody provided by embodiments of the present invention and sequences necessary for protein expression.

The present invention also provides a pharmaceutical composition comprising the antibody described in any one of the above, and the pharmaceutical composition provided by the present invention may only contain any one or a combination of at least two of the antibodies provided in the embodiments.

It should be clear to those skilled in the art that, for pharmaceutical compositions, a pharmaceutically acceptable excipient is also included. Conventional excipients required to make powders or tablets and other dosage forms should be used as ingredients that should be added in the pharmaceutical process.

The present invention also provides a method for detecting whether CLDN exists in a biological sample, which comprises:

a step of administering an antibody according to any one of the above to a biological sample, wherein the antibody has a detectable label, and a step of detecting the presence or content of the detectable label.

Pharmacodynamic Test in Animal a) Tumor tissues were collected from gastric cancer xenograft model GA0006 tumor-bearing mice, and cut into tumor masses with a diameter of 2-3 mm, which were inoculated subcutaneously at the right anterior scapula of Balb/c nude mice.
b) When the average tumor volume of Balb/c nude mice reached about 100 mm$^3$, the mice were randomly divided into different groups (6 mice in each group). All animals were weighed, and the tumor volume was measured with vernier caliper. According to the tumor volume, random grouping method was adopted to ensure that the tumor volume among different groups was similar. The coefficient of variation (CV) of tumor volume in each group was calculated by the formula CV=SD/MTV×100%, which should be less than 40%.

Random grouping was done using StudyDirector™. The grouping day was DO, and the administration was started on the same day. The detailed administration method, dosage and route of administration are shown in the table below.

TABLE 2

| | | Administration parameters of animal pharmacodynamic test | | | |
| --- | --- | --- | --- | --- | --- |
| Group | Number of animals | Administration group | Dose (mg/kg) | Mode of administration | Administration cycle |
| 1 | 6 | Vehicle control | — | i.p. | BIW × 4 weeks |
| 2 | 6 | QP192193 | 10 | i.p. | BIW × 4 weeks |
| 3 | 6 | QP207208 | 10 | i.p. | BIW × 4 weeks |
| 4 | 6 | QP11151116 | 10 | i.p. | BIW × 4 weeks |
| 5 | 6 | IMAB362 | 10 | i.p. | BIW × 4 weeks |

The dosage volume was 10 μL/g.

The meaning of antibody numbers in Tables 1 and 2, such as QP190191, denotes a combination of a heavy chain and a light chain.

c) After starting the administration, the body weight and tumor volume of mice were measured twice a week.

The formula of calculation tumor volume: Tumor volume $(mm^3)=\frac{1}{2}\times(a\times b^2)$ (wherein, a denotes the long diameter and b denotes the short diameter). The experiment was terminated one week after the last administration, the mice were sacrificed, and the tumors were taken out, weighed, and photographed. The following analysis methods are selected for data analysis:

Relative tumor proliferation rate, T/C (%), that is, the percentage value of relative tumor volume or tumor weight between the treatment group and the control group at a certain time point. The calculation formula is: T/C %=TRTV/CRTV×100% (TRTV: average RTV of the treatment group; CRTV: average RTV of the control group; RTV=Vt/V0, V0 is the tumor volume of the animal at the time of grouping, and Vt is the tumor volume of the animals after treatment).

The relative tumor inhibition rate, TGI (%), is calculated as TGI %=(1-T/C)×100% (T and C are the relative tumor volume (RTV) of the treatment group and the control group at a certain time point, respectively).

The mean tumor volume of mice in PBS control group was 911.16±177.81 mm$^3$ on the 31st day after administration. The mean tumor volume of the antibodies QP192193 (10 mg/kg), QP207208 (10 mg/kg) and QP11151116 (10 mg/kg) was 580.97±67.97 mm$^3$, 680.28±193.50 mm$^3$, and 722.38±118.07 mm$^3$ on the 31st day after administration, respectively. The TGI of that was 36.34%, 25.34% and 20.72%, respectively. The mean tumor volume of control molecule IMAB362 (10 mg/kg) was 661.28±104.49 mm$^3$ on the 31st day after administration, and TGI was 27.42% (see the table below). All three screened molecules inhibited tumor growth to a certain extent, although there was no statistically significant difference. QP192193 showed a trend that it was better than the control molecule IMAB362, and QP207208 and QP11151116 also showed the same level of tumor inhibition ability as IMAB362. Moreover, the body weight of mice did not decrease significantly during the administration process, indicating that antibody molecules had no obvious toxic and side effects on mice.

| Groups | D0 Tumor Volume/mm$^3$ | D31 tumor volume/mm$^3$ | TGI % | P value (t test) |
|---|---|---|---|---|
| PBS | 116.33 | 911.16 | — | — |
| QP192193 | 116.11 | 580.97 | 41.52% | 0.11 |
| QP207208 | 116.06 | 680.28 | 29.01% | 0.40 |
| IMAB362 | 116.34 | 661.28 | 31.44% | 0.25 |
| QP11151116 | 116.22 | 722.38 | 23.74% | 0.40 |

The analysis results of tumor weight are similar to those of tumor volume. The average tumor weight of mice in PBS control group was 722.57±176.32 mg on the 31st day after administration. The average tumor weights of the antibody molecules QP192193, QP207208, and QP11151116 treatment groups were 455.5±46.42 mg, 391.93±111.15 mg and 432.03±66.25 mg on the 31st day after the end of administration, respectively, and the TGI was 36.96%, 45.76% and 40.21%, respectively. The average tumor weight of control molecule IMAB362 treatment group was 435.78±91 mg on the 31st day after administration, and the TGI was 39.69%. (See the table below)

| Groups | D31 tumor weight/g | TGI/% | P value (t test) |
|---|---|---|---|
| PBS | 0.722 | — | — |
| QP192193 | 0.455 | 36.96% | 0.26 |
| QP207208 | 0.392 | 45.76% | 0.12 |
| IMAB362 | 0.436 | 39.69% | 0.21 |
| QP11151116 | 0.432 | 40.21% | 0.20 |

Therefore, through the PDX animal pharmacodynamic test, we found that the selected antibody molecule antibody molecule had better or the same level of tumor suppressing ability in vivo than the control molecule IMAB362.

The experimental results are shown in FIGS. 9 to 14, in which the results of the pharmacodynamic test of antibody against gastric cancer PDX model GA0006 are shown in FIG. 9. FIG. 10A is the tumor growth curve of PBS group (negative control) after grouping. FIG. 10B is the tumor growth curve of QP192193 group after grouping. FIG. 10C is the tumor growth curve of QP207208 group after grouping. FIG. 10D is the tumor growth curve of QP11151116 group after grouping. FIG. 10E is the tumor growth curve of the control antibody IMAB362 group after grouping. FIG. 11 shows the weight of tumor at D31 in each group of mice added with each antibody of the present invention and a control antibody. FIG. 12 is a real shot diagram of the tumor volume of each experimental group. FIG. 13 is the body weight curve of mice in each group. FIG. 14 is the curve of body weight change rate of mice in each group. It can be seen from the experimental results that the invented antibody exhibits a better effect on inhibiting tumor growth than IMAB362 in animal pharmacodynamics in vivo.

The invention claimed is:

1. An anti-CLDN18.2 antibody or active fragment thereof which comprises a heavy chain and a light chain:

the heavy chain contains three CDRs, represented by HCDR1, HCDR2, and HCDR3, respectively;

the light chain contains three CDRs, represented by LCDR1, LCDR2, and LCDR3, respectively;

and the amino acid sequence of the anti-CLDN18.2 antibody or active fragment thereof comprises a combination of the CDRs:

HCDR1 comprising SEQ ID No: 47, HCDR2 comprising SEQ ID No: 48, and HCDR3 comprising SEQ ID No: 49; and LCDR1 comprising SEQ ID No: 50, LCDR2 comprising SEQ ID No: 51, and LCDR3 comprising SEQ ID No: 52.

2. The anti-CLDN18.2 antibody or active fragment thereof according to claim 1, wherein the heavy chain of the antibody comprises SEQ ID No: 7; or the light chain of the antibody comprises SEQ ID No: 14.

3. The anti-CLDN18.2 antibody or active fragment thereof according to claim 1, wherein the heavy chain of the antibody comprises SEQ ID No: 7 and the light chain of the antibody comprises SEQ ID No: 14.

4. A polynucleotide encoding the antibody or active fragment thereof according to claim 1.

5. A pharmaceutical composition comprising the antibody or active fragment thereof according to claim 1.

6. A method of detecting the presence of CLDN18.2 in a biological sample, which comprises:

a step of administering the antibody or active fragment thereof according to claim 1 to a biological sample, wherein the antibody has a detectable label;

and a step of detecting whether the detectable label is present or detecting the content of the detectable label.

7. A method of treating CLDN18.2-expressing tumors, which comprises a step of administering a therapeutically effective amount of the antibody or active fragment thereof according to claim 1 to a subject in need thereof.

* * * * *